(12) United States Patent
Zheng et al.

(10) Patent No.: US 7,220,832 B2
(45) Date of Patent: May 22, 2007

(54) DERMACENTOR VARIABILIS GABA-GATED CHLORIDE CHANNELS

(75) Inventors: Yingcong Zheng, Colonia, NJ (US); Doris F. Cully, Scotch Plains, NJ (US); Steve W. Ludmerer, North Wales, PA (US)

(73) Assignee: Merck & Co., Inc, Rahway, NJ (US)

( * ) Notice: Subject to any disclaimer, the term of this patent is extended or adjusted under 35 U.S.C. 154(b) by 785 days.

(21) Appl. No.: 10/239,956

(22) PCT Filed: Mar. 28, 2001

(86) PCT No.: PCT/US01/09955

§ 371 (c)(1), (2), (4) Date: Sep. 25, 2002

(87) PCT Pub. No.: WO01/74884

PCT Pub. Date: Oct. 11, 2001

(65) Prior Publication Data

US 2003/0208041 A1 Nov. 6, 2003

Related U.S. Application Data

(60) Provisional application No. 60/193,791, filed on Mar. 31, 2000.

(51) Int. Cl.
C07K 14/705 (2006.01)
(52) U.S. Cl. .................................... 530/350
(58) Field of Classification Search ............... None
See application file for complete search history.

(56) References Cited

U.S. PATENT DOCUMENTS

| 5,487,976 | A | 1/1996 | Soderlund et al. |
| 5,527,703 | A | 6/1996 | Cully et al. |
| 5,661,035 | A | 8/1997 | Tsien et al. |
| 5,693,492 | A | 12/1997 | Cully et al. |
| 5,767,261 | A | 6/1998 | Wingate et al. |
| 5,852,188 | A | 12/1998 | Cook |
| 5,854,002 | A | 12/1998 | Tomalski et al. |
| 5,859,221 | A | 1/1999 | Cook et al. |
| 6,008,046 | A | 12/1999 | Ffrench-Constant et al. |

FOREIGN PATENT DOCUMENTS

| WO | WO 93/07161 | 4/1993 |
| WO | WO 98/02582 | 1/1998 |
| WO | WO 98/49185 | 11/1998 |

OTHER PUBLICATIONS

Henderson, J. et al. "PCR-Based Homology Probing Reveals a Family of GABA Receptor-Like Genes in *Drosophila melanogaster*", Insect Biochemistry and Molecular Biology, 1994, vol. 24, pp. 363-371.
Accession No. M69057, Inv. Apr. 26, 1993.
Accession No. O17145, Created Jan. 1, 1998.
Accession No. O18469, Created Jan. 1, 1998.
Chen, R. et al. "Cloning and functional expression of a *Drosophila* γ-aminobutyric acid receptor", Proc. Natl. Acad. Sci. USA, 1994, vol. 91, pp. 6069-6073.
ffrench-Constant, R. et al. "*Drosophila* γ-Aminobutyric Acid Receptor Gene *Rdl* Shows Extensive Alternative Splicing", Journal of Neurochemistry, 1993, vol. 60, pp. 2323-2326.
Bass, B. "RNA editing and hypermutation by adenosine deamination", Trends in Biochemical Sciences, 1997, vol. 22, pp. 157-162.
Buckingham, S. et al. "Actions of agonists and convulsant antagonists on a *Drosophila melanogaster* GABA receptor (Rdl) homo-oligomer expressed in *Xenopus* oocytes", Neuroscience Letters, 1994, vol. 181, pp. 137-140.
Cupp, E. "Biology of Ticks", Veterinary Clinics of North America: Small Animal Practice, 1991, vol. 21, pp. 1-26.
Ffrench-Constant, R. et al. "A point mutation in a *Drosophila* GABA receptor confers insecticide resistance", Nature, 1993, vol. 363, pp. 449-451.
Ffrench-Constant, R. et al. "Molecular cloning and transformation of cyclodiene resistance in *Drosophila*: An invertebrate γ-aminobutyric acid subtype A receptor locus", Proc. Natl. Acad. Sci. USA, 1991, vol. 88, pp. 7209-7213.
Gonzalez, J. et al. "Improved indicators of cell membrane potential that use fluorescence resonance energy transfer", Chemistry & Biology, 1997, vol. 4, pp. 269-277.
Hanrahan, C. et al. "RNA Editing of *Drosophila* Sodium Channel Gene", Annals NY Academy of Sciences, 1999, vol. 868, pp. 51-66.
Hosie, A. et al. "Actions of the insecticide fipronil, on dieldrin-sensitive and—resistant GABA receptors of *Drosophila melanogaster*", British Journal of Pharmacology, 1995, vol. 115, pp. 909-912.
Millar, N. et al. "Stable expression of a functional homo-oligomeric *Drosophila* GABA recptor in a *Drosophila* cell line", Proc. R. Soc. Lond. B, 1994, vol. 258, pp. 307-314.
Olsen, R. et al. "Molecular biology of $GABA_A$ receptors", FASEB J., 1990, vol. 4, pp. 1469-1480.
Rauh, J. et al. "Pharmacological and biochemical properties of insect GABA receptors", Trends in Pharmacological Sciences, 1990, vol. 11, pp. 325-329.
Smith, A. et al. "Benzodiazepine modulation of recombinant $\alpha 1\beta 3\gamma 2$ $GABA_A$ receptor function efficacy determination using the Cytosensor microphysiometer", European Journal of Pharmacology, 1998, vol. 359, pp. 261-269.

*Primary Examiner*—Michael Pak
(74) *Attorney, Agent, or Firm*—Heidi M. Struse; Jack Tribble; Sheldon O. Heber

(57) ABSTRACT

The present invention features *Dermacentor variabilis* GABA-gated chloride channel polypeptides and nucleic acids, and uses of such polypeptides and nucleic acids. *D. variabilis* is a widely distributed tick associated with different diseases. A preferred use of the present invention is to obtain compounds for preventing or treating a tick infestation.

2 Claims, 8 Drawing Sheets

```
clone9      MR......QA.MAFSCWSFVLFVAVAVTSAGRDNGPAPLRPG..Q..TQRG.....QNIT
clone8      MR......QA.MAFSCWSFVLFVAVAVTSAGRDNGPAPLRPG..Q..TQRG.....QNIT
clone5-1    MR......QA.MAFSCWSFVLFVAVAVTSAGRDNGPAPLRPG..Q..TQRG.....QNIT
Drosrdl     MSDSKMDKLARMAPLPRTPLLTIWLAINMALIAQETGHKRIHTVQAATGGGSMLGDVNIS clone9      QILNAFFTRGYDRRVRPNYGGVPVEVGVTMQIISISTVSEVQMDFTSDFYFRQSWRDERL
clone8      QILNAFFTRGYDRRVRPNYGGVPVEVGVTMQIISISTVSEVQMDFTSDFYFRQSWRDERL
clone5-1    QILNAFFTRGYDRRVRPNYGGVPVEVGVTMQIISISTVSEVQMDFTSDFYFRQSWRDERL
Drosrdl     AILDSFSVS.YDKRVRPNYGGPPVEVGVTMYVLSISSVSEVLMDFTLDFYFRQFWTDPRL clone9      SFQKSPDLESMTVGAEVAERIWVPDTFFANEKSAYFHAATTPNTFLRIGSGGEVFRSIRL
clone8      SFQKSPDLESMTVGAEVAERIWVPDTFFANEKSAYFHAATTPNTFLRIGSGGEVFRSIRL
clone5-1    SFQKSPDLESMTVGAEVAERIWVPDTFFANEKSAYFHAATTPNTFLRIGSGGEVFRSIRL
Drosrdl     AYRKRPGVETLSVGSEFIKNIWVPDTFFVNEKQSYFHIATTSNEFIRVHHSGSITRSIRL clone9      TVTASCPMDLRYFPMDRQACTIEIESFGYTMKDIRYRWSDGDTSVRIAKEVELPQFKVLG
clone8      TVTASCPMDLRYFPMDRQACTIEIESFGYTMKDIRYRWSDGDTSVRIAKEVELPQFKVLG
clone5-1    TVTAGCPMDLRYFPMDRQACTIEIESFGYTMKDIRYRWSDGDTSVRIAKEVELPQFKVLG
Drosrdl     TITASCPMNLQYFPMDRQLCHIEIESFGYTMRDIRYFWRDGLSSVGMSSEVELPQFRVLG clone9      HVQKAKEVALTTGNYSRLVCEIRFARSMGYYLIQIYIPAGLIVVISWVSFWLHRNASPAR
clone8      HVQKAKEVALTTGNYSRLVCEIRFARSMGYYLIQIYIPAGLIVVISWVSFWLHRDASPAR
clone5-1    HVQKAKEVALTTGNYSRLVCEIRFARSMGYYLIQIYIPAGLIVVISWVSFWLHRDASPAR
Drosrdl     HRQRATEINLTTGNYSRLACEIQFVRSMGYYLIQIYIPSGLIVVISWVSFWLNRNATPAR clone9      VALGVTTVLTMTTLMSSTNAALPKISYVKSIDVYLGTCFVMVFTALLEYAAVGYLGKRIT
clone8      VALGVTTVLTMTTLMSSTNAALPKISYVKSIDVYLGTCFVMVFTALLEYAAVGYLGKRIT
clone5-1    VALGVTTVLTMTTLMSSTNAALPKISYVKSIDVYLGTCFVMVFTALLEYAAVGYLGKRIT
Drosrdl     VALGVTTVLTMTTLMSSTNAALPKISYVKSIDVYLGTCFVMVFASLLEYATVGYMAKRIQ clone9      MRKTRCQQLAKLAEQHRQRCAAASSNEPSSEP.LLASPEVSIVKTVGSCQVCPAAVASQG
clone8      MRKTRCQQLAKLAEQHRQRCAAASSNEPSSEP.LLASPEVSIVKTVGSCQVCPAAVASQG
clone5-1    MRKTRCQQLAKLAEQHRQRCAAASSNEPSSEP.LLASPEVSIVKTVGSCRVCPAAVASQG
Drosrdl     MRKQRFMAIQKIAEQKKQQLDGA..NQQQANPNPNAN..VGGPGGVG...VGPGGP...G clone9      QPREAPPTGFTMGRRGADQCCPGLQGSCQVCPAA....VA......SQTQQQAPPPG..I
clone8      QPREAPPTGFTMGRRGADQCCPGLQGSCQVCPAA....VA......SQTQQQAPPPG..I
clone5-1    QPREAPPTGFTMGRRGADQCCPGLQGSCQVCPAA....VA......SQTQQQAPPPG..I
Drosrdl     GPGGGVNVGVGMGMGPEHGHGHGHHAHSHGHPHAPKQTVSNRPIGFSNIQQNVGTRGCSI clone9      P....MEVRLKMVDPKGFSKSSTLENTVNG...AP.........................
clone8      P....MEVRLKMVDPKGFSKSSTLENTVNG...AP.........................
clone5-1    P....MEVRLKMVDPKGFSKSSTLENTVNG...AP.........................
Drosrdl     VGPLFQEVRFKVHDPKAHSKGGTLENTVNGGRGGPQSHGPGPGQGGGPPGGGGGGGGGGG clone9      ......DIEAAF..........CKNPNKLFGVGPSDIDKYSRVVFPVCFVCFDLMYWIIY
clone8      ......DIEAAF..........CKNPNKLFGVGPSDIDKYSRVVFPVCFVCFDLMYWIIY
clone5-1    ......GIEAAF..........CKNPNKLFGVGPSDIDKYSRVVFPVCFVCFGLMYWIIY
Drosrdl     PPEGGGDPEAAVPAHLLHPGKVKKDINKLLGITPSDIDKYSRIVFPVCFVCFNLMYWIIY clone9      LHISDVLPDDVGDD...
clone8      LHISDVLPDDVGDD...
clone5-1    LHVSDVLPDDVGDD...
Drosrdl     LHVSDVVADDLVLLGEE
```

Fig. 1

SEQ. ID. NO. 5 x SEQ. ID. NO. 8 DNA Alignment

Percent Similarity: 58.101   Percent Identity: 58.101

Match display thresholds for the alignment(s):
| = IDENTITY
: = 5
. = 1

```
  1 ........................................ATGAG   5
                                             |
  1 ATGAGTGATTCAAAAATGGACAAGCTGGCCCGGATGGCGCCCCTGCCCCG  50

6 ACAAGCGATGGCGTTCAGTTGCTGGTCCTTCGTTCTCTTCGTGGCCGTCG  55
    | || ||      || ||   | || ||     |    | ||     |
 51 CACACCGCTGCTAACCATCTGGCTGGCCATCAACATGGCCCTGATTGCAC 100

56 CTGTCACCAGTGCCGGTCGG...GATAATGGTCCAGCCCCCTGCGGCCG  102
    | || ||  |     |||    |||  |    |   |||  |
101 AGGAAACGGGCCACAAACGGATCCATACAGTGCAAGCGGCGACTGGCGGT 150

103 GGACAAACGCAACGTGGACAAAACATCACGCAGATTCTGAATGCCTTCTT 152
    ||    | ||   |||      |||||| |     |||||  | || |||
151 GGCAGCATGCTGGGTGACGTAAACATATCCGCTATTCT...CGACTCCTT 197

153 TACACGTGGGTACGACAGGAGGGTGAGGCCAAATTATGGCGGCGTTCCAG 202
    ||     |  | || |||||||  || ||     |||||  | ||||
198 TAGTGTTAGTTACGACAAAAGAGTAAGACCCAATTACGGTGGTCCCCCTG 247

203 TGGAAGTTGGCGTCACTATGCAGATTATCAGCATAAGTACAGTCTCTGAA 252
    |||| |||||||||||  |  ||| |||||| ||    |||| || |||
248 TGGAGGTTGGCGTCACAATGTATGTCCTCAGTATCAGTTCGGTTTCGGAA 297

253 GTACAAATGGACTTTACTTCTGACTTCTATTTCCGGCAATCGTGGCGGGA 302
    || | |||||||||| |  |||||   ||||    || ||    ||| ||
298 GTTCTAATGGACTTCACATTGGATTTTTACTTTCGTCAATTTTGGACCGA 347

303 CGAGCGACTCTCGTTCCAGAAAAGCCCAGACCTCGAGAGCATGACTGTGG 352
    |  |  |||   ||| |  |    ||||| ||   | |     ||| |
348 TCCTCGTTTAGCGTATAGAAAACGACCTGGTGTAGAAACACTATCGGTTG 397

353 GCGCTGAAGTGGCCGAGAGGATCTGGGTACCCGACACCTTCTTCGCCAAC 402
    |  | ||  |       |||  || ||||||||  ||||| |   |
398 GATCAGAGTTCATTAAGAATATTTGGGTACCTGACACCTTTTTTGTAAAT 447

403 GAGAAGAGCGCCTACTTTCATGCGGCCACAACGCCCAACACTTTCCTCCG 452
    | | |      |   || |||||||  || ||    | || ||| |||
448 GAAAAACAATCATATTTTCACATTGCAACAACCAGTAATGAATTCATACG 497

453 CATCGGCTCCGGAGGAGAGGTTTTCCGCAGTATTCGACTGACGGTGACTG 502
    |       ||| ||    |  ||||||  ||  || ||    |  || |
498 TGTGCATCATTCTGGATCGATAACAAGAAGTATTAGATTGACTATAACCG 547

503 CCAGCTGCCCAATGGATCTCAGATACTTCCCGATGGACAGACAAGCGTGC 552
    |   || || ||| ||||   |||  ||| ||||| |  |    ||||
548 CATCGTGTCCGATGAATCTACAATATTTCCCCATGGATCGCCAGCTGTGC 597

553 ACTATAGAGATAGAAAGCTTTGGTTATACCATGAAAGACATCCGCTACCG 602
    || || || ||||||||| |||||||| || ||| ||| |||||||||
598 CACATTGAAATCGAAAGCTTCGGTTACACGATGCGAGATATCCGATATTT 647

603 GTGGTCGGACGGTGACACGTCCGTCCGCATCGCCAAGGAGGTAGAGTTGC 652
    |||  || ||    |  ||  |||| || ||||| ||| |||
648 CTGGAGAGATGGACTGAGTAGTGTTGGCATGAGCAGTGAGGTCGAACTAC 697
```

Fig. 2A

```
 653 CGCAGTTCAAGGTCCTCGGTCACGTCCAAAAAGCCAAAGAGGTTGCCCTA  702
     ||||||||  ||  |  || |||  ||  |   ||  |   ||  |    ||||
 698 CGCAGTTCCGAGTTTTGGGACACAGGCAGAGGGCGACCGAAATAAACCTA  747

703 ACGACAGGAAACTACTCCCGCCTGGTATGTGAAATACGGTTCGCCCGCTC  752
     ||  ||||||  |||||  ||  ||  | |  || ||||||  |  || ||
 748 ACCACAGGCAACTATTCGCGTTTAGCCTGCGAAATTCAGTTCGTGCGTTC  797

753 CATGGGCTACTACCTGATCCAGATCTACATCCCGGCCGGATTGATCGTGG  802
     ||||||||||||||  ||  ||  ||||||||  ||  |  |||  |||||||||  |
 798 GATGGGCTACTACCTTATACAAATCTACATACCCTCTGGACTGATCGTTG  847

803 TTATTTCCTGGGTCTCCTTTTGGCTCCACCGTAACGCTAGTCCAGCTCGC  852
     ||||  ||  ||||||  ||  ||||||||||  |  ||  ||  |   ||  ||  ||
 848 TTATATCATGGGTATCATTTTGGCTCAATCGCAATGCAACGCCGGCGCGT  897

853 GTCGCGCTCGGCGTCACCACCGTGCTCACGATGACCACACTCATGTCCAG  902
     ||  ||||||  ||||||  ||||||||  |  ||||||||    |  |||||
 898 GTGGCGCTCGGTGTGACAACCGTGTTGACAATGACCACTTTGATGTCGTC  947

903 TACCAACGCAGCGCTGCCCAAAATATCCTACGTCAAGAGTATCGACGTCT  952
     ||  ||  ||||||||||||||  ||  ||  ||  ||||||||  ||  ||||||||
 948 AACAAATGCAGCGCTGCCAAAGATTTCGTACGTCAAATCGATTGACGTCT  997

953 ACCTGGGCACATGTTTCGTAATGGTGTTTACCGCGCTCCTGGAGTACGCC  1002
     | ||||||  |||||| |||||||   |||  ||  ||  ||||| ||||||
 998 ATCTGGGAACATGCTTCGTTATGGTCTTTGCCAGTCTACTGGAATACGCC  1047

1003 GCGGTAGGATATCTCGGCAAGAGAATCACCATGAGGAAAACCCGCTGTCA  1052
     ||||  ||  ||  |  ||  |||  |||  |  ||| | | |    | | |
1048 ACGGTCGGCTACATGGCAAAACGAATTCAAATGCGAAAACAAAGATTTAT  1097

1053 GCAGCTGGCAAAACTTGCAGAGCAACACAGGCAGAGATGCGCCGCAGC.T  1101
     |  |  |   |||  |  || ||  ||  |  |  |  |||  || || |||
1098 GGCGATCCAAAAGATAGCCGAACAGAAAAAGCAACAGCTCGACGGAGCGA  1147

1102 TCTTCCAACGAGCCAAGCTCTGAGCCCTTGCTAGCCAGTCCTGAAGTATC  1151
     |  ||  ||  |||  |    |  ||  |     |  |    |
1148 ACCAACAGCAGGCGAATCCCAATCCCAATGCAAATGTGGGCGGACCCGGA  1197

1152 CATTGTCAAGACGGTCGGTTCCTGTCAAGTTTGTCCTGCTGCGGTGGCAT  1201
     |  |||   |    |     |||  |   |||| | ||
1198 GGAGTGGGCGTTGGACCCGGCGGACCCGGAGGACCCGGTGGCGGGGTCAA  1247

1202 CCCAAGGACAACCGAGGGAA..GCACCACCAACCGGATTTACCATGGGTC  1249
         |          |||| |  |||| | ||      ||| |
1248 TGTGGGCGTCGGTATGGGCATGGGACCGGAACATGGCCACGGGCATGGAC  1297

1250 GCAGAGGCGCAGACCAATGTTGCCCTGGTCTCCAGGGTTCATGTCAGGTC  1299
      | |  ||  |||  |  ||  |   |  |  |   |
1298 ACCACGCCCACAGCCATGGACATCCGCATGCGCCCAAGCAAACAGTGAGT  1347

1300 TGCCCCGCTGCGGTCGCCTCACAAACCCAACAACAGGCTCCTCCACCAGG  1349
     ||||    ||  ||   |  |  |||||||| | | |||  ||
1348 AACCGCCCAATCGGCTTTTCCAATATCCAACAAAACGTTGGTACGCGCGG  1397

1350 GATACCTAT.................GGAAGTACGTCTCAAAATGGTTG  1381
     |  ||              |||  ||  |||||  |
1398 TTGCTCGATAGTGGGACCCTTGTTCCAGGAGGTGAGATTCAAGGTCCACG  1447

1382 ACCCCAAGGGATTCAGCAAATCCTCGACTCTGGAGAACACCGTCAACGGC  1431
     ||||  ||||     |   |||    |  ||  ||||||||||  ||  ||  |||
1448 ACCCGAAGGCCCACTCCAAGGGCGGAACGCTGGAGAATACGGTGAATGGC  1497
```

Fig. 2B

```
1432 ...................................................GCGCCGG 1438
                                                        ||| |||
1498 GGACGCGGTGGTCCGCAATCGCATGGACCGGGTCCGGGCCAAGGCGGCGG 1547

1439 ACATCGAGGCAGCG.................................... 1452
     || |   ||| | |
1548 ACCGCCCGGCGGTGGCGGAGGCGGTGGAGGCGGGGGCGGACCGCCCGAGG 1597

1453 ...TTTTGCAAGAACCCCAACAAATTATTTGGCGTCGGCCCTTCCGATAT 1499
        |||  ||  ||||||  |  | ||| ||   || ||||||  ||
1648 AAAGTAAAAAAGGACATCAACAAGCTGCTGGGCATCACGCCCTCCGACAT 1697

1500 CGACAAGTACTCCCGAGTGGTGTTCCCCGTTTGCTTCGTCTGTTTCGACC 1549
     |||||||||||  ||  |  |||||||||||  |||||  ||  ||| |||
1698 CGACAAGTACTCACGCATCGTGTTCCCCGTGTGCTTTGTGTGCTTCAACC 1747

1550 TCATGTACTGGATCATTTACCTGCACATCAGCGACGTTCTGCCGGACGA. 1598
     | |||||||||||||||||||||||  |||||||||||  |  | || ||
1748 TGATGTACTGGATCATTTACCTGCATGTCAGCGACGTGGTCGCCGATGAT 1797

1599 ........CGTCGGCGACGACTAG 1614
             |  ||||||  ||  |||
1798 CTGGTGCTTCTGGGCGAGGAGTAG 1821
```

Fig. 2C

SEQ. ID. NO. 6 ATGAGACAAGCGATGGCGTTCAGTTGCTGGTCCTTCGTTCTCTTCGTGGCCGTCGCTGTC
SEQ. ID. NO. 4 ATGAGACAAGCGATGGCGTTCAGTTGCTGGTCCTTCGTTCTCTTCGTGGCCGTCGCTGTC
SEQ. ID. NO. 5 ATGAGACAAGCGATGGCGTTCAGTTGCTGGTCCTTCGTTCTCTTCGTGGCCGTCGCTGTC

SEQ. ID. NO. 6 ACCAGTGCCGGTCGGGATAATGGTCCAGCCCCCCTGCGGCCGGGACAAACGCAACGTGGA
SEQ. ID. NO. 4 ACCAGTGCCGGTCGGGATAATGGTCCAGCCCCCCTGCGGCCGGGACAAACGCAACGTGGA
SEQ. ID. NO. 5 ACCAGTGCCGGTCGGGATAATGGTCCAGCCCCCCTGCGGCCGGGACAAACGCAACGTGGA

SEQ. ID. NO. 6 CAAAACATCACGCAGATTCTGAATGCCTTCTTTACACGTGGGTACGACAGGAGGGTGAGG
SEQ. ID. NO. 4 CAAAACATCACGCAGATTCTGAATGCCTTCTTTACACGTGGGTACGACAGGAGGGTGAGG
SEQ. ID. NO. 5 CAAAACATCACGCAGATTCTGAATGCCTTCTTTACACGTGGGTACGACAGGAGGGTGAGG

SEQ. ID. NO. 6 CCAAATTATGGCGGCGTTCCAGTGGAAGTTGGCGTCACTATGCAGATTATCAGCATAAGT
SEQ. ID. NO. 4 CCAAATTATGGCGGCGTTCCAGTGGAAGTTGGCGTCACTATGCAGATTATCAGCATAAGT
SEQ. ID. NO. 5 CCAAATTATGGCGGCGTTCCAGTGGAAGTTGGCGTCACTATGCAGATTATCAGCATAAGT

SEQ. ID. NO. 6 ACAGTCTCTGAAGTACAAATGGACTTTACTTCTGACTTCTATTTCCGGCAATCGTGGCGG
SEQ. ID. NO. 4 ACAGTCTCTGAAGTACAAATGGACTTTACTTCTGACTTCTATTTCCGGCAATCGTGGCGG
SEQ. ID. NO. 5 ACAGTCTCTGAAGTACAAATGGACTTTACTTCTGACTTCTATTTCCGGCAATCGTGGCGG

SEQ. ID. NO. 6 GACGAGCGACTCTCGTTCCAGAAAAGCCCAGACCTCGAGAGCATGACTGTGGGCGCTGAA
SEQ. ID. NO. 4 GACGAGCGACTCTCGTTCCAGAAAAGCCCAGACCTCGAGAGCATGACTGTGGGCGCTGAA
SEQ. ID. NO. 5 GACGAGCGACTCTCGTTCCAGAAAAGCCCAGACCTCGAGAGCATGACTGTGGGCGCTGAA

SEQ. ID. NO. 6 GTGGCCGAGAGGATCTGGGTACCCGACACCTTCTTCGCCAACGAGAAGAGCGCCTACTTT
SEQ. ID. NO. 4 GTGGCCGAGAGGATCTGGGTACCCGACACCTTCTTCGCCAACGAGAAGAGCGCCTACTTT
SEQ. ID. NO. 5 GTGGCCGAGAGGATCTGGGTACCCGACACCTTCTTCGCCAACGAGAAGAGCGCCTACTTT

SEQ. ID. NO. 6 CATGCGGCCACAACGCCCAACACTTTCCTCCGCATCGGCTCCGGAGGAGAGGTTTTCCGC
SEQ. ID. NO. 4 CATGCGGCCACAACGCCCAACACTTTCCTCCGCATCGGCTCCGGAGGAGAGGTTTTCCGC
SEQ. ID. NO. 5 CATGCGGCCACAACGCCCAACACTTTCCTCCGCATCGGCTCCGGAGGAGAGGTTTTCCGC

SEQ. ID. NO. 6 AGTATTCGACTGACGGTGACTGCCGGCTGCCCAATGGATCTCAGATACTTCCCGATGGAC
SEQ. ID. NO. 4 AGTATTCGACTGACGGTGACTGCCAGCTGCCCAATGGATCTCAGATACTTCCCGATGGAC
SEQ. ID. NO. 5 AGTATTCGACTGACGGTGACTGCCAGCTGCCCAATGGATCTCAGATACTTCCCGATGGAC

SEQ. ID. NO. 6 AGACAAGCGTGCACTATAGAGATAGAAAGCTTTGGTTATACCATGAAAGACATCCGCTAC
SEQ. ID. NO. 4 AGACAAGCGTGCACTATAGAGATAGAAAGCTTTGGTTATACCATGAAAGACATCCGCTAC
SEQ. ID. NO. 5 AGACAAGCGTGCACTATAGAGATAGAAAGCTTTGGTTATACCATGAAAGACATCCGCTAC

SEQ. ID. NO. 6 CGGTGGTCGGACGGTGACACCTCCGTCCGCATCGCCAAGGAGGTAGAGTTGCCGCAGTTC
SEQ. ID. NO. 4 CGGTGGTCGGACGGTGACACCTCCGTCCGCATCGCCAAGGAGGTAGAGTTGCCGCAGTTC
SEQ. ID. NO. 5 CGGTGGTCGGACGGTGACACGTCCGTCCGCATCGCCAAGGAGGTAGAGTTGCCGCAGTTC

SEQ. ID. NO. 6 AAGGTCCTCGGTCACGTCCAAAAAGCCAAAGAGGTTGCCCTAACGACAGGAAACTACTCC
SEQ. ID. NO. 4 AAGGTCCTCGGTCACGTCCAAAAAGCCAAAGAGGTTGCCCTAACGACAGGAAACTACTCC
SEQ. ID. NO. 5 AAGGTCCTCGGTCACGTCCAAAAAGCCAAAGAGGTTGCCCTAACGACAGGAAACTACTCC

SEQ. ID. NO. 6 CGCCTGGTATGTGAAATACGGTTCGCCCGCTCCATGGGCTACTACCTGATCCAGATCTAC
SEQ. ID. NO. 4 CGCCTGGTATGTGAAATACGGTTCGCCCGCTCCATGGGCTACTACCTGATCCAGATCTAC
SEQ. ID. NO. 5 CGCCTGGTATGTGAAATACGGTTCGCCCGCTCCATGGGCTACTACCTGATCCAGATCTAC

SEQ. ID. NO. 6 ATCCCGGCCGGATTGATCGTGGTTATTTCCTGGGTCTCCTTTTGGCTCCACCGTGACGCT
SEQ. ID. NO. 4 ATCCCGGCCGGATTGATCGTGGTTATTTCCTGGGTCTCCTTTTGGCTCCACCGTGACGCT
SEQ. ID. NO. 5 ATCCCGGCCGGATTGATCGTGGTTATTTCCTGGGTCTCCTTTTGGCTCCACCGTAACGCT

Fig. 3A

SEQ. ID. NO. 6 AGTCCAGCTCGCGTCGCGCTCGGCGTCACCACCGTGCTCACGATGACCACACTCATGTCC
SEQ. ID. NO. 4 AGTCCAGCTCGCGTCGCGCTCGGCGTCACCACCGTGCTCACGATGACCACACTCATGTCC
SEQ. ID. NO. 5 AGTCCAGCTCGCGTCGCGCTCGGCGTCACCACCGTGCTCACGATGACCACACTCATGTCC

SEQ. ID. NO. 6 AGTACCAACGCAGCGCTGCCCAAAATATCCTACGTCAAGAGTATCGACGTCTACCTGGGC
SEQ. ID. NO. 4 AGTACCAACGCAGCGCTGCCCAAAATATCCTACGTCAAGAGTATCGACGTCTACCTGGGC
SEQ. ID. NO. 5 AGTACCAACGCAGCGCTGCCCAAAATATCCTACGTCAAGAGTATCGACGTCTACCTGGGC

SEQ. ID. NO. 6 ACATGTTTCGTAATGGTGTTTACCGCGCTCCTGGAGTACGCCGCGGTAGGATATCTCGGC
SEQ. ID. NO. 4 ACATGTTTCGTAATGGTGTTTACCGCGCTCCTGGAGTACGCCGCGGTAGGATATCTCGGC
SEQ. ID. NO. 5 ACATGTTTCGTAATGGTGTTTACCGCGCTCCTGGAGTACGCCGCGGTAGGATATCTCGGC

SEQ. ID. NO. 6 AAGAGAATCACCATGAGGAAAACCCGCTGTCAGCAGCTGGCAAAACTTGCAGAGCAACAC
SEQ. ID. NO. 4 AAGAGAATCACCATGAGGAAAACCCGCTGTCAGCAGCTGGCAAAACTTGCAGAGCAACAC
SEQ. ID. NO. 5 AAGAGAATCACCATGAGGAAAACCCGCTGTCAGCAGCTGGCAAAACTTGCAGAGCAACAC

SEQ. ID. NO. 6 AGGCAGAGATGCGCCGCGGCTTCTTCCAACGAGCCAAGCTCTGAGCCCTTGCTAGCCAGT
SEQ. ID. NO. 4 AGGCAGAGATGCGCCGCGGCTTCTTCCAACGAGCCAAGCTCTGAGCCCTTGCTAGCCAGT
SEQ. ID. NO. 5 AGGCAGAGATGCGCCGCAGCTTCTTCCAACGAGCCAAGCTCTGAGCCCTTGCTAGCCAGT

SEQ. ID. NO. 6 CCTGAGGTATCCATTGTCAAGACGGTCGGTTCCTGTCGGGTTTGTCCTGCTGCGGTGGCA
SEQ. ID. NO. 4 CCTGAAGTATCCATTGTCAAGACGGTCGGTTCCTGTCAAGTTTGTCCTGCTGCGGTGGCA
SEQ. ID. NO. 5 CCTGAAGTATCCATTGTCAAGACGGTCGGTTCCTGTCAAGTTTGTCCTGCTGCGGTGGCA

SEQ. ID. NO. 6 TCCCAAGGACAACCGAGGGAAGCACCACCAACCGGATTTACCATGGGTCGCAGAGGCGCA
SEQ. ID. NO. 4 TCCCAAGGACAACCGAGGGAAGCACCACCAACCGGATTTACCATGGGTCGCAGAGGCGCA
SEQ. ID. NO. 5 TCCCAAGGACAACCGAGGGAAGCACCACCAACCGGATTTACCATGGGTCGCAGAGGCGCA

SEQ. ID. NO. 6 GACCAATGTTGCCCTGGTCTCCAGGGTTCATGTCAGGTCTGCCCCGCTGCGGTCGCCTCA
SEQ. ID. NO. 4 GACCAATGTTGCCCTGGTCTCCAGGGTTCATGTCAGGTCTGCCCCGCTGCGGTCGCCTCA
SEQ. ID. NO. 5 GACCAATGTTGCCCTGGTCTCCAGGGTTCATGTCAGGTCTGCCCCGCTGCGGTCGCCTCA

SEQ. ID. NO. 6 CAAACCCAACAACAGGCTCCTCCACCAGGGATACCTATGGAAGTACGTCTCAAAATGGTT
SEQ. ID. NO. 4 CAAACCCAACAACAGGCTCCTCCACCAGGGATACCTATGGAAGTACGTCTCAAAATGGTT
SEQ. ID. NO. 5 CAAACCCAACAACAGGCTCCTCCACCAGGGATACCTATGGAAGTACGTCTCAAAATGGTT

SEQ. ID. NO. 6 GACCCCAAGGGATTCAGCAAATCCTCGACTCTGGAGAACACCGTCAACGGCGCGCCGGGC
SEQ. ID. NO. 4 GACCCCAAGGGATTCAGCAAATCCTCGACTCTGGAGAACACCGTCAACGGCGCGCCGGAC
SEQ. ID. NO. 5 GACCCCAAGGGATTCAGCAAATCCTCGACTCTGGAGAACACCGTCAACGGCGCGCCGGAC

SEQ. ID. NO. 6 ATCGAGGCAGCGTTTTGCAAGAACCCCAACAAATTATTTGGCGTCGGCCCTTCCGATATC
SEQ. ID. NO. 4 ATCGAGGCAGCGTTTTGCAAGAACCCCAACAAATTATTTGGCGTCGGCCCTTCCGATATC
SEQ. ID. NO. 5 ATCGAGGCAGCGTTTTGCAAGAACCCCAACAAATTATTTGGCGTCGGCCCTTCCGATATC

SEQ. ID. NO. 6 GACAAGTACTCCCGAGTGGTGTTCCCCGTTTGCTTCGTCTGTTTCGGCCTCATGTACTGG
SEQ. ID. NO. 4 GACAAGTACTCCCGAGTGGTGTTCCCCGTTTGCTTCGTCTGTTTCGACCTCATGTACTGG
SEQ. ID. NO. 5 GACAAGTACTCCCGAGTGGTGTTCCCCGTTTGCTTCGTCTGTTTCGACCTCATGTACTGG

SEQ. ID. NO. 6 ATCATTTACCTGCACGTCAGCGACGTTCTGCCGGACGACGTCGGCGACGACTAG
SEQ. ID. NO. 4 ATCATTTACCTGCACATCAGCGACGTTCTGCCGGACGACGTCGGCGACGACTAG
SEQ. ID. NO. 5 ATCATTTACCTGCACATCAGCGACGTTCTGCCGGACGACGTCGGCGACGACTAG

Fig. 3B

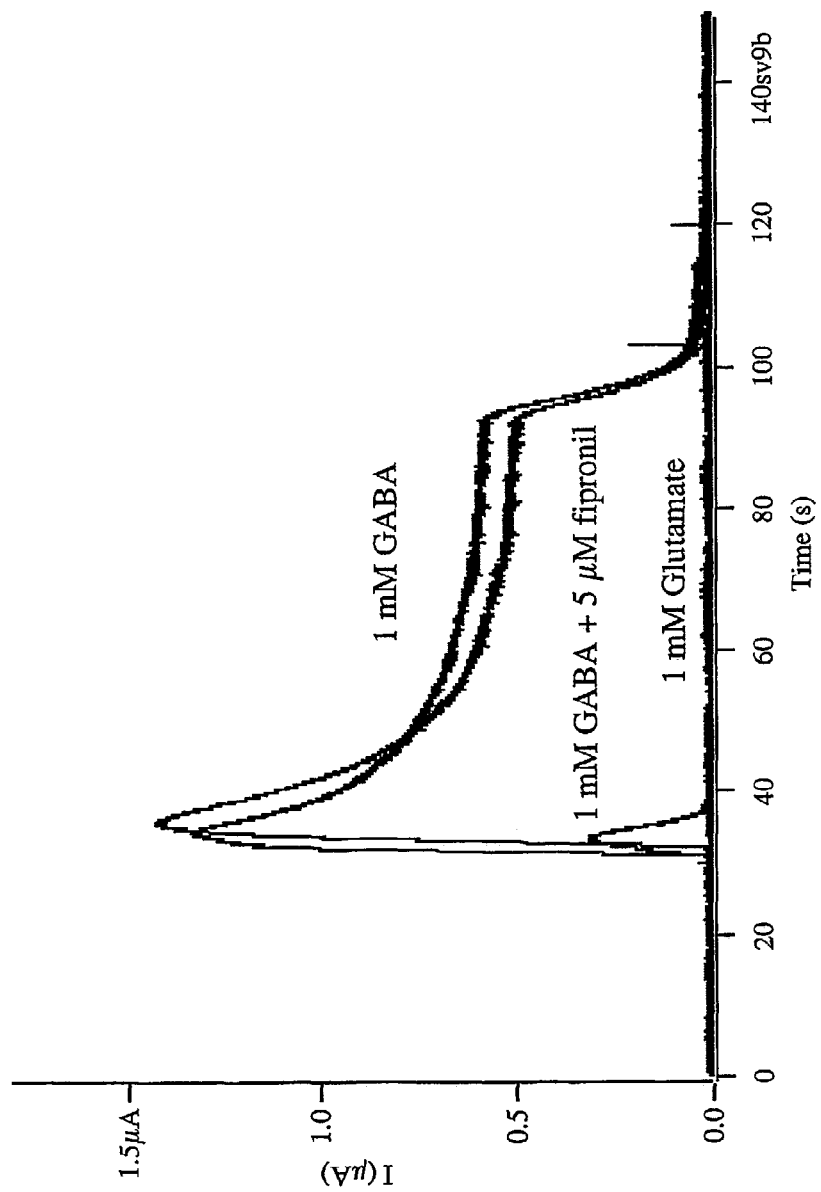

DERMACENTOR VARIABILIS GABA-GATED CHLORIDE CHANNELS

CROSS-REFERENCE TO RELATED APPLICATIONS

The present application claims priority to provisional application U.S. Ser. No. 60/193,791, filed Mar. 31, 2000, hereby incorporated by reference herein.

BACKGROUND OF THE INVENTION

The references cited herein are not admitted to be prior art to the claimed invention.

γ-Aminobutric acid (GABA) is a major inhibitory neurotransmitter present in insects and vertebrates. Vertebrate central nervous system GABA receptors have been divided into subtype $GABA_A$ and subtype $GABA_B$. $GABA_A$ receptors give rise to GABA gated $Cl^-$ currents and contain modulatory sites for benzodiazepines, barbiturates and steroids. $GABA_B$ receptors mediate effects of GABA on $K^+$ and $Ca^{2+}$ conductances through interactions with G proteins. (Rauh et al., *TiPS* 11:325-329, 1990.)

Nucleic acid encoding for GABA receptors have been cloned from different sources including vertebrates and insects. Examples of some vertebrate GABA receptors are discussed by Olsen et al., *FASEB J.* 4:1469-1480, 1990. Examples of insect GABA receptor are provided in Soderlund et al., U.S. Pat. No. 5,487,976, Tomalski et al., U.S. Pat. No. 5,854,002, Wingate et al., U.S. Pat. No. 5,767,262 and Roush et al., International Publication Number WO 93/07161.

An example of a GABA receptor obtained from an insect is the dieldrin resistant GABA receptor (Rdl). Nucleic acid encoding for Rdl has been cloned from *Drosophila*. (Ffrench-Constant et al., *Proc. Natl. Acad. Sci. USA* 88:7209-7213, 1991, and Roush et al., International Publication Number WO 93/07161.) Insects containing an A302S mutation in the rdl gene are resistant to different GABA antagonists including cyclodienes, picrotoxinin and fibronil. (Ffrench-Constant et al., *Nature* 363:449-451, 1993; Buckingham et al., *Neuroscience Letters* 181:137-140, 1994; and Hosie et al., *British Journal of Pharmacology* 115:909-912, 1995.)

SUMMARY OF THE INVENTION

The present invention features *Dermacentor variabilis* GABA-gated chloride channel polypeptides and nucleic acids, and uses of such polypeptides and nucleic acids. *D. variabilis* is a widely distributed tick associated with different diseases. A preferred use of the present invention is to obtain compounds for preventing or treating a tick infestation.

*D. variabilis* GABA-gated chloride channel polypeptides contain a region of at least 9 contiguous amino acids that is present in SEQ. ID. NOs. 1, 2 or 3. SEQ. ID. NOs. 1, 2 and 3 are derived from the same gene. Differences between these sequences are due to mRNA editing and strain variations.

*D. variabilis* GABA-gated chloride channel nucleic acids contain a region encoding for a *D. variabilis* GABA-gated chloride channel polypeptide or containing at least 18 contiguous nucleotides that is present in SEQ. ID. NOs. 4, 5, 6 or the complement thereof. The effect of mRNA editing and strain variations also accounts for the differences in the encoding nucleic acids of SEQ. ID. NOs. 4, 5 and 6.

Thus, a first aspect of the present invention describes a purified polypeptide comprising a unique amino acid region of a *D. variabilis* GABA-gated chloride channel. The unique region is at least 9 amino acids in length.

A "unique amino acid region" is a region of contiguous amino acids present in SEQ. ID. NOs. 1, 2 or 3 that is not present in SEQ. ID. NO. 7. SEQ. ID. NO. 7 is a *D. melaizogaster* Rdl sequence. Reference to the unique region being present in SEQ. ID. NOs. 1, 2 or 3 includes unique regions that are present in any combination of SEQ. ID. NOs. 1, 2 and 3. The unique region may contain segments of contiguous amino acids present in SEQ. ID. NO. 7 smaller than the indicated unique region size.

A "purified polypeptide" represents at least about 10% of the total protein present in a sample or preparation. In preferred embodiments, the purified polypeptide represents at least about 50%, at least about 75%, or at least about 95% of the total protein in a sample or preparation. Reference to "purified polypeptide" does not require that the polypeptide has undergone any purification and may include, for example, chemically synthesized polypeptide that has not been purified.

Another aspect of the present invention describes a purified nucleic acid comprising a nucleotide sequence encoding for a unique amino acid region of a *D. variabilis* GABA-gated chloride channel. The encoded for region is at least 9 amino acids in length.

A "purified nucleic acid" represents at least about 10% of the total nucleic acid present in a sample or preparation and includes both single-stranded and double-stranded nucleic acid. In preferred embodiments, the purified nucleic acid represents at least about 50%, at least about 75%, or at least about 95% of the total nucleic acid in a sample or preparation. Reference to "purified nucleic acid" does not require that the nucleic acid has undergone any purification and may include, for example, chemically synthesized nucleic acid that has not been purified.

Another aspect of the present invention describes a purified nucleic acid comprising a unique nucleotide sequence region of a *D. variabilis* GABA-gated chloride channel nucleic acid or the complement thereof. The unique nucleotide sequence region is at least 18 nucleotides in length.

A "unique nucleotide sequence region" is a region that comprises at least 18 contiguous nucleotides of SEQ. ID. NOs. 4, 5, 6 or the complement thereof, that is not present in SEQ. ID. NO. 8 or the complement thereof. SEQ. ID. NO. 8 is the nucleotide sequence encoding for a *D. melanogaster* Rdl sequence. Reference to the unique region being present in SEQ. ID. NOs. 4, 5, 6 or the complement thereof, includes unique regions that are present in any combination of SEQ. ID. NOs. 4, 5 and 6 or the complement thereof. The unique region may contain segments of contiguous nucleotides present in SEQ. ID. NO. 8 smaller than the indicated unique region size.

Another aspect of the present invention describes an expression vector. The expression vector comprises a recombinant nucleotide sequence encoding for a unique amino acid region of a *D. variabilis* GABA-gated chloride channel.

A "recombinant nucleotide sequence" is a sequence that is present on a nucleic acid containing one or more nucleic acid regions not naturally associated with that sequence. Examples of nucleic acid regions that may be present include one or more regulatory elements not naturally associated with the sequence, viral elements, and selectable markers.

Another aspect of the present invention describes a recombinant cell comprising an expression vector encoding for a *D. variabilis* GABA-gated chloride channel. The expression vector contains a promoter functionally coupled to nucleic acid encoding for a unique region of a *D. variabilis* GABA-gated chloride channel and is recognized by an RNA polymerase present in the cell.

Another aspect of the present invention describes a recombinant cell made by introducing an expression vector encoding for a unique amino acid region of a *D. variabilis* GABA-gated chloride channel into a cell. The GABA-gated chloride channel nucleic acid present in the expression vector can be inserted into the host genome or can exist apart from the host genome.

Another aspect of the present invention features a purified antibody preparation comprising an antibody that binds to a *D. variabilis* GABA-gated chloride channel. A "purified antibody preparation" is a preparation where at least about 10% of the antibodies present bind to a *D. variabilis* GABA-gated chloride channel. In preferred embodiments, antibodies binding to a *D. variabilis* GABA-gated chloride channel represent at least about 50%, at least about 75%, or at least about 95% of the total antibodies present. Reference to "purified antibody preparation" does not require that the antibodies in the preparation have undergone any purification.

Another aspect of the present invention describes a method of producing a *D. variabilis* GABA-gated chloride channel polypeptide. The method involves the step of incubating a cell containing a recombinant nucleotide sequence encoding for a *D. variabilis* GABA-gated chloride channel polypeptide under conditions where the polypeptide is expressed.

Another aspect of the present invention describes a method for assaying the binding of a compound to a *D. variabilis* GABA-gated chloride channel. The assay involves the following: (a) expressing a polypeptide comprising a unique *D. variabilis* GABA-gated chloride channel amino acid sequence region from a recombinant nucleotide sequence; (b) providing to the polypeptide a test preparation comprising one or more test compounds; and (c) measuring the ability of the test preparation to bind to the polypeptide.

Another aspect of the present invention describes a method of measuring GABA-gated chloride channel activity. The method measures the effect of a compound on GABA-gated chloride channel activity in a recombinant cell that expresses a functional GABA-gated chloride channel from a recombinant nucleotide sequence.

Another aspect of the present invention describes a method of decreasing or preventing a tick infestation. The method involves the following: (a) identifying a compound that modulates *D. variabilis* GABA-gated chloride channel activity; and (b) using the compound to decrease or prevent a tick infestation.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 illustrates a comparison of *D. variabilis* GABA-gated chloride channel polypeptides of SEQ. ID. NOs. 1 (clone 8), 2 (clone 9), and 3 (clone 5), along with *D. melanogaster* Rdl (SEQ. ID. NO. 7).

FIGS. 2A-2C illustrate a comparison of nucleic acid encoding a *D. variabilis* GABA-gated chloride channel (SEQ. ID. NO. 5) with nucleic acid encoding for *D. melanogaster* rdl (SEQ. ID. NO. 8).

FIGS. 3A and 3B illustrate a sequence comparison of SEQ. ID. NOs. 4, 5 and 6.

FIG. 5 illustrates the sensitivity of the *D. variabilis* GABA-gated chloride channel to fibronil. Activity was measured using the *D. variabilis* GABA-gated chloride channel of SEQ. ID. NO. 2.

DETAILED DESCRIPTION OF THE INVENTION

Figure 4:
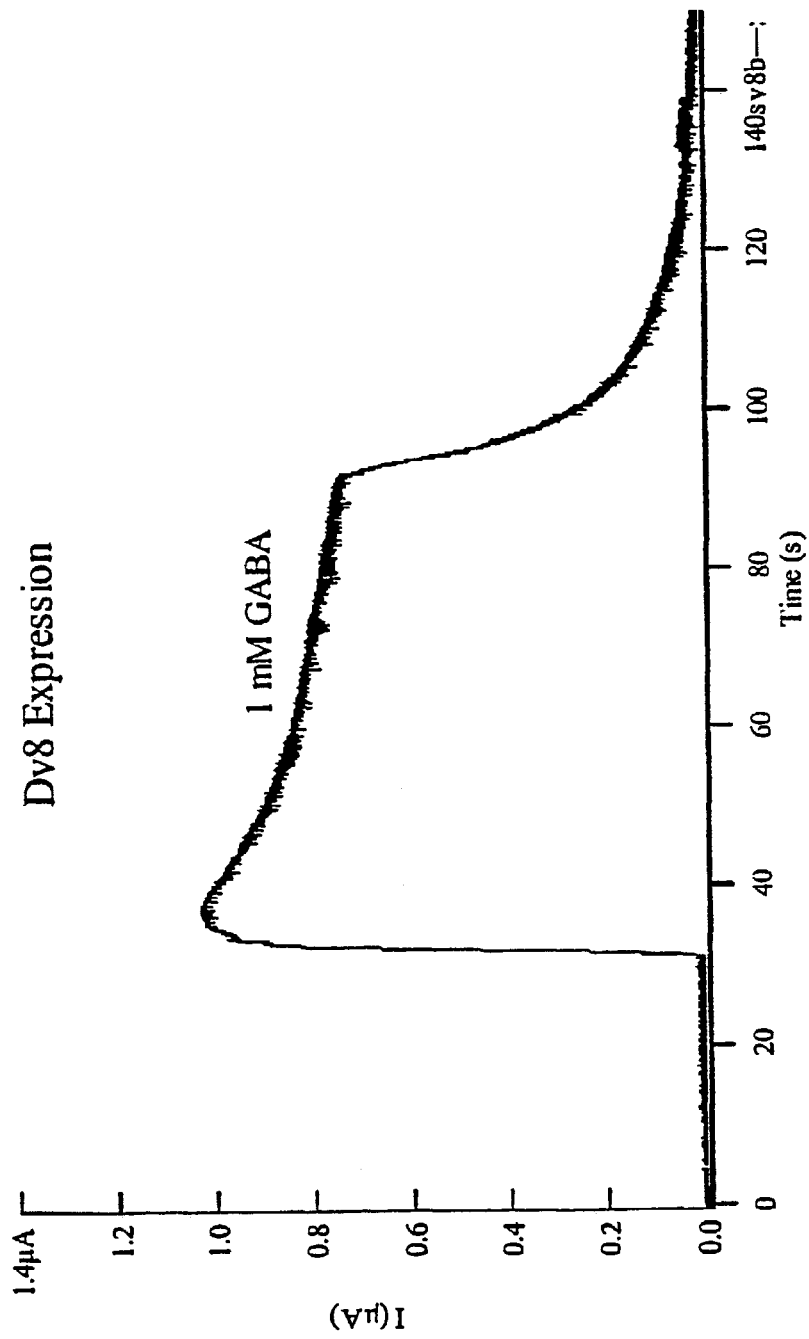
FIG. 4 illustrates *D. variabilis* GABA-gated chloride channel activity. Activity was measured using the *D. variabilis* GABA-gated chloride channel of SEQ. ID. NO. 1.

The present application identifies *D. variabilis* GABA-gated chloride channels amino acid and nucleic acid sequences. Such identification provides targets that can be used, for example, to identify *D. variabilis* and to obtain compounds useful for treating or preventing a *D. variabilis* infestation.

Throughout its life cycle *D. variabilis* feeds on the blood of different hosts and can act as a disease carrier. As a result of its blood feeding activities *D. variabilis* has been linked to a variety of different diseases including Rocky Mountain spotted fever, babesiosis, tick paralysis, anaplasmosis, tularemia, and cytauxzoonosis. Hosts for *D. variabilis* include humans, dogs, cattle, horses, deer, and other wild and domesticated animals. (See, for example, Cupp, Biology of Ticks. In Hoskins (ed.): Tick-Transmitted Diseases W.B. Saunders Company, 1991, p. 1-26.)

Identifying *D. variabilis* can be achieved using nucleic acid sequences and antibodies distinguishing *D. variabilis* GABA-gated chloride channel nucleic acids or polypeptides from the nucleic acid or polypeptide of other organisms. Determining the presence of *D. variabilis* can be used to track the spread of the parasite.

Compounds useful for treating or preventing a *D. variabilis* infestation exert a toxic effect on the parasite without exerting an unacceptable toxic effect on the environment, or on humans and other mammals. The *D. variabilis* GABA-gated chloride channels provides an attractive target for obtaining compounds achieving such effects. Advantages of using *D. variabilis* GABA-gated chloride channels to screen for useful compounds include the differences between GABA-gated chloride channels found in ticks and in mammals, and the identification of a site that can be targeted to achieve a toxic effect in *D. variabilis*.

*D. variabilis* GABA-gated chloride channel active compounds modulate the activity of the channel by, for example, acting as agonists, antagonists, or allosteric modulators. Compounds identified as modulating *D. variabilis* GABA-gated chloride channel activity can be further tested to determine their ability to exert a toxic effect on *D. variabilis*. Such compounds can be readily counter screened against human or mammalian GABA-gated chloride channels to identify those compounds more likely to have an undesirably effect on a human or other mammals.

Compounds active at *D. variabilis* GABA-gated chloride channels may also exert toxic effects on other ticks or related parasites such as mites, and may be useful for preventing the spread of disease associated with such parasites. Additionally, using the present invention as guide, GABA receptors related to the *D. variabilis* GABA-gated chloride channels can be obtained from other organisms. The GABA-gated chloride channels from related organisms can be used in conjunction with the *D. variabilis* GABA-gated chloride channel to facilitate the screening of more broadly active compounds.

*D. Variabilis* GABA-Gated Chloride Channel Polypeptides

*D. variabilis* GABA-gated chloride channel polypeptides contain a *D. variabilis* GABA-gated chloride channel amino acid region. Such polypeptides may contain additional regions present, or not present, in SEQ. ID. NOs. 1, 2, or 3.

Unique *D. variabilis* GABA-gated chloride channel amino acid regions can readily be identified based on a comparison of the *D. variabilis* GABA-gated chloride channel sequences described herein with the *D. melanogaster* Rdl sequence. FIG. 1 provides a sequence comparison of SEQ. ID. NO. 1, 2, 3 and 7.

In different embodiments a *D. variabilis* GABA-gated chloride channel polypeptide comprises or consists of a unique amino acid region. Examples of unique regions include the following:

| | |
|---|---|
| QILNAFFTRG; | (SEQ. ID. NO. 9) |
| MTVGAEVAERIWVP; | (SEQ. ID. NO. 10) |
| RWSDGDTSVRIAK; | (SEQ. ID. NO. 11) |
| TALLEYAAVGYLG; | (SEQ. ID. NO. 12) |
| RCAAASSNEPSSEPLLASPEVSIVKT; | (SEQ. ID. NO. 13) |
| QPREAPPTGFT; | (SEQ. ID. NO. 14) |
| MGRRGADQCCPGLQGSCQVC; | (SEQ. ID. NO. 15) |
| MEVRLKMVDPKGFSKSS; | (SEQ. ID. NO. 16) |
| HISDVLPDDVGDD; and | (SEQ. ID. NO. 17) |
| HVSDVLPDDVGDD. | (SEQ. ID. NO. 18) |

The definition of unique amino acid region is with respect to the *D. melanogaster* Rdl sequence. Thus, for example, a unique amino acid region may be present in one or more *D. variabilis* GABA-gated chloride channels and in polypeptides from one or more organisms other than *D. melanogaster*. Examples of other organisms where a unique *D. variabilis* GABA-gated chloride channel amino acid region may be present include related organisms such as other ticks and/or other arachnids.

*D. variabilis* GABA-gated chloride channel polypeptides have a variety of uses, such as providing a component for a functional channel; being used as an antigen to produce antibodies binding to a *D. variabilis* GABA-gated chloride channel; being used as a target to identify compounds binding to a *D. variabilis* GABA-gated chloride channel; and/or being used in assays to measure the ability of a compound to effect *D. variabilis* GABA-gated chloride channel activity.

Chimeric polypeptides containing one or more regions from a *D. variabilis* GABA-gated chloride channel and one or more regions not from a *D. variabilis* GABA-gated chloride channel can be produced based on the disclosure provided herein. Region(s) not from a *D. variabilis* GABA-gated chloride channel can be used, for example, to achieve a particular purpose or to produce a polypeptide that can substitute for a *D. variabilis* GABA-gated chloride channel or a fragment thereof. Particular purposes that can be achieved by additional regions present in chimeric *D. variabilis* GABA-gated chloride channel polypeptides include providing a marker for isolation, facilitating functional analysis of different channel regions, and enhancing an immune response.

In different embodiments a *D. variabilis* GABA-gated chloride channel polypeptide comprises or consists of a unique amino acid region at least 18, at least 27, or at least 54, amino acids in length. Preferably, the *D. variabilis* GABA-gated chloride channel related polypeptide comprises or consists of the amino acid sequence of SEQ. ID. NOs. 1, 2 or 3.

*D. variabilis* GABA-gated chloride channel polypeptides also include a functional GABA-gated chloride channel having a sequence similarity to SEQ. ID. NO. 1 of at least about 70%, at least about 80%, at least about 90%, or at least about 95%. Sequence similarity for polypeptides can be determined by using procedures such as the Smith and Waterman Bestfit Algorithm with gap weight, 8; length weight 2; and by BLAST (Altschul, et al., 1997. *Nucleic Acids Res*. 25, 3389-3402, hereby incorporated by reference herein). In one embodiment sequence similarity is determined using tBLASTn search program with the following parameters: MATRIX:BLOSUM62, PER RESIDUE GAP COST: 11, and Lambda ratio: 1.

Polypeptides can be produced using standard techniques including those involving chemical synthesis and those involving biochemical synthesis. Techniques for chemical synthesis of polypeptides are well known in the art. (See, for example, Vincent, in *Peptide and Protein Drug Delivery*, New York, N.Y., Dekker, 1990.)

Biochemical synthesis techniques for polypeptides are also well known in the art. Such techniques employ a nucleic acid template for polypeptide synthesis. The genetic code providing the sequences of nucleic acid triplets coding for particular amino acids is well known in the art. (See, e.g., Lewin *GENES IV*, p. 119, Oxford University Press, 1990.) Examples of techniques for introducing nucleic acid into a cell and expressing the nucleic acid to produce protein are provided in references such as Ausubel, *Current Protocols in Molecular Biology*, John Wiley, 1987-1998, and Sambrook et al., in *Molecular Cloning, A Laboratory Manual*, 2$^{nd}$ Edition, Cold Spring Harbor Laboratory Press, 1989.

Functional *D. Variabilis* GABA-Gated Chloride Channel

The identification of the amino acid and nucleic acid sequences of a *D. variabilis* GABA-gated chloride channel provides tools for obtaining functional channels related to the *D. variabilis* GABA-gated chloride channel from other sources such as other ticks and mites. Such identification also provides a starting point for producing functional derivatives of SEQ. ID. NOs. 1, 2 or 3.

The amino acid and nucleic acid sequence information from *D. variabilis* GABA-gated chloride channel can be used to help identify and obtain *D. variabilis* GABA-gated chloride channel polypeptides and related peptides using different techniques. For example, SEQ. ID. NO. 1 can be used to design degenerative nucleic acid probes or primers to identify and clone nucleic acid encoding for a *D. variabilis* GABA-gated chloride channel related polypeptide; and SEQ. ID. NO. 4 or fragments thereof, can be used under conditions of moderate stringency to identify and clone nucleic acid encoding *D. variabilis* GABA-gated chloride channel related polypeptides.

The use of degenerative probes and moderate stringency conditions for cloning is well known in the art. Examples of such techniques are described by Ausubel, *Current Protocols in Molecular Biology*, John Wiley, 1987-1998, and Sambrook et al., in *Molecular Cloning, A Laboratory Manual*, 2$^{nd}$ Edition, Cold Spring Harbor Laboratory Press, 1989.

Starting with a *D. variabilis* GABA-gated chloride channel obtained from a particular source derivatives can be produced having functional activity. Such derivatives include polypeptides with amino acid substitutions, additions and deletions. Some examples of suitable substitutions are provided by a comparison of SEQ. ID. NOs. 1, 2 and 3. The ability of a polypeptide to have *D. variabilis* GABA-gated chloride channel activity can be confirmed using techniques such as those measuring GABA-gated chloride channel activity.

Differences in naturally occurring amino acids are due to different R groups. An R group effects different properties of the amino acid such as physical size, charge and hydrophobicity. Amino acids can be divided into different groups as follows: neutral and hydrophobic (alanine valine, leucine, isoleucine, proline, tryptophan, phenylalaine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide functioning.

Changes outside of different amino acids groups can also be made. Preferably, such changes are made taking into account the position of the amino acid to be substituted in the polypeptide. For example, arginine can substitute more freely for nonpolar amino acids in the interior of a polypeptide then glutamate because of its long aliphatic side chain. (See, Ausubel, *Current Protocols in Molecular Biology*, John Wiley, 1987-1998, Supplement 33 Appendix 1C.)

*D. Variabilis* GABA-Gated Chloride Channel Antibodies

Antibodies recognizing *D. variabilis* GABA-gated chloride channel antibodies can be produced using a polypeptide containing SEQ. ID. NOs. 1, 2, 3 or a fragment thereof as an antigen. Preferably, a polypeptide used as an antigen consists of a polypeptide of SEQ. ID. NOs. 1, 2, or 3 or a fragment thereof at least 9 amino acids in length. In an embodiment of the present invention, the polypeptide consists of the amino acid sequence of SEQ. ID. NO. 19 (LGKRITMRKTRCQQLAKLAEQHRQR).

Antibodies to *D. variabilis* GABA-gated chloride channel have different uses such as being used to identify the presence of a *D. variabilis* GABA-gated chloride channel and to isolate *D. variabilis* GABA-gated chloride channel polypeptides. Identifying the presence of a *D. variabilis* GABA-gated chloride channel can be used, for example, to identify cells producing a *D. variabilis* GABA-gated chloride channel and to distinguish such cells from cells of other organisms.

Techniques for producing and using antibodies are well known in the art. Examples of such techniques are described in Ausubel, *Current Protocols in Molecular Biology*, John Wiley, 1987-1998, Harlow et al., *Antibodies, A Laboratory Manual*, Cold Spring Harbor Laboratory, 1988, and Kohler et al., *Nature* 256:495-497, 1975.

Binding Assay

*D. variabilis* GABA-gated chloride channel or a fragment thereof can be used in studies to identify compounds binding to the channel. Such studies can be performed using different formats including competitive and non-competitive formats. Competition studies can be carried out using compounds known to bind to the channel or after identifying a compound binding to the channel. Examples of compounds that bind to *D. variabilis* GABA-gated chloride channel include GABA and fibronil.

Based on the disclosure provided herein procedures measuring binding to a GABA-gated chloride channel from other organisms can be adapted for use with *D. variabilis* GABA-gated chloride channel polypeptides. An example of a procedure measuring binding to a GABA-gated chloride channel is provided by Millar et al., *Proc. R. Soc. Lond. B.* 258:307-314, 1994.

A particular *D. variabilis* GABA-gated chloride channel sequence involved in ligand binding can be readily identified by using labeled compounds that bind to a portion of the channel. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding to a compound can be subdivided to further locate the binding region. Fragments used for binding studies can be generated using recombinant nucleic acid techniques.

Preferably, binding studies are performed using *D. variabilis* GABA-gated chloride channel expressed from a recombinant nucleic acid. More preferably, recombinantly expressed *D. variabilis* GABA-gated chloride channel consists of the amino acid sequences of SEQ. ID. NOs. 1, 2, or 3.

Binding assays can be performed using individual compounds or preparations containing different numbers of compounds. A preparation containing different numbers of compounds having the ability to bind to the *D. variabilis* GABA-gated chloride channel can be divided into smaller groups of compounds that can be tested to identify the compound(s) binding to the channel. In an embodiment of the present invention a test preparation containing at least 10 compounds is used in a binding assay.

Recombinantly produced *D. variabilis* GABA-gated chloride channels used in binding assays can be present in different environments. Such environments include, for example, cell extracts and purified cell extracts containing the *D. variabilis* GABA-gated chloride channel; and also include, for example, the use of a purified *D. variabilis* GABA-gated chloride channel polypeptide produced by recombinant means which is introduced into a different environment.

Functional Assays

*D. variabilis* GABA-gated chloride channel functional assays measure one or more ligand-gated chloride channel activities where the channel is made up in whole, or in part, by the *D. variabilis* GABA-gated chloride channel. *D. variabilis* GABA-gated chloride channel activity can be measured using the channel described herein by itself; or as a subunit in combination with one or more additional ligand-gated chloride channel subunits (preferably one or more GABA-gated chloride channel subunits), where the subunits combine together to provide functional channel activity.

Assays measuring GABA-gated chloride channel activity include functional screening using $^{36}Cl$, functional screening using patch clamp electrophysiology and functional screening using fluorescent dyes. Techniques for carrying out such assays in general are well known in the art. (See, for example, Smith et al., *European Journal of Pharmacology* 159:261-269, 1998, González and Tsien, *Chemistry & Biology* 4:269-277, 1997; Millar et al., *Proc. R. Soc. Lond. B*. 258:307-314, 1994; Rauh et al., *TiPS* 11:325-329, 1990; and Tsien et al., U.S. Pat. No. 5,661,035.)

Functional assays can be performed using individual compounds or preparations containing different compounds. A preparation containing different compounds where one or more compounds affect *D. variabils* GABA-gated chloride channel activity can be divided into smaller groups of compounds to identify the compound(s) affecting *D. variabilis* GABA-gated chloride channel activity. In an embodiment of the present invention a test preparation containing at least 10 compounds is used in a functional assay.

Recombinantly produced *D. variabilis* GABA-gated chloride channel present in different environments can be used in a functional assay. Suitable evironments include live cells and purified cell extracts containing the *D. variabilis* GABA-gated chloride channel and an appropriate membrane for activity; and the use of a purified *D. variabilis* GABA-gated chloride channel produced by recombinant means that is introduced into a different environment suitable for measuring GABA-gated chloride channel activity.

*D. variabilis* GABA-gated chloride channel derivatives can be used to assay for compounds active at the channel and to obtain information concerning different regions of the channel. For example, GABA-gated chloride channel derivatives can be produced where amino acid regions in the native channel are altered and the effect of the alteration on channel activity can be measured to obtain information regarding different channel regions.

D. Variabilis GABA-Gated Chloride Channel Nucleic Acid

*D. variabilis* GABA-gated chloride channel nucleic acids contain a region encoding for a *D. variabilis* GABA-gated chloride channel polypeptide or containing at least 18 contiguous nucleotides that is present in SEQ. ID. NOs. 4, 5, 6 or the complement thereof. Such nucleic acids may contain additional regions present, or not present, in nucleic acid encoding for *D. variabilis* GABA-gated chloride channel or in SEQ. ID. NOs. 4, 5, 6 or the complement thereof.

Unique nucleic acid regions can readily be identified by comparing the nucleic acid sequences of SEQ. ID. NOs. 4, 5, and 6 with the nucleic acid sequence of SEQ. ID. NO. 8. FIGS. 2A-2C illustrate a comparison of the nucleic acid sequence of SEQ. ID. NO. 5 with SEQ. ID. NO. 8. The comparison provided in FIGS. 2A-2C can readily be extended to take into account SEQ. ID. NOs. 4 and 6. As illustrated in FIGS. 3A and 3B, SEQ. ID. NOs. 4, 5, and 6 are very similar.

In different embodiments a nucleic acid comprises or consists of a unique nucleotide sequence region from a *D. variabilis* GABA-gated chloride channel. Examples of unique regions include the following:

| | |
|---|---|
| CAAACGCAACGTGGACAA; | (SEQ. ID. NO. 20) |
| GAGCGACTCTCGTTCCAG; | (SEQ. ID. NO. 21) |

-continued

| | |
|---|---|
| ATCGGCTCCGGAGGAGAG; | (SEQ. ID. NO. 22) |
| AAGGTCCTCGGTCACGTCCAAAAA; | (SEQ. ID. NO. 23) |
| CTCGGCAAGAGAATCACC; | (SEQ. ID. NO. 24) |
| GGTTCCTGTCAAGTTTGT; | (SEQ. ID. NO. 25) |
| GGTTCCTGTCGGGTTTGT; and | (SEQ. ID. NO. 26) |
| CCAACCGGATTTACCATG. | (SEQ. ID. NO. 27) |

The definition of unique nucleotide sequence region is with respect to *D. melanogaster* rdl nucleic acid. Thus, for example, a unique nucleotide sequence region may be present in nucleic acids encoding for one or more *D. variabilis* GABA-gated chloride channels and encoding for polypeptides from one or more organisms other than *D. melanogaster*. Examples of other organisms where a unique *D. variabilis* GABA-gated chloride channel nucleotide sequence region may be present include related organisms such as other ticks.

*D. variabilis* GABA-gated chloride channel nucleic acid have a variety of uses, such as being used as a hybridization probe or PCR primer to identify the presence of *D. variabilis* GABA-gated chloride channel nucleic acid; being used as a hybridization probe or PCR primer to identify nucleic acid encoding for a GABA receptor related to the *D. variabilis* GABA-gated chloride channel; and/or being used for recombinant expression of *D. variabilis* GABA-gated chloride channel polypeptides.

Regions may be present in *D. variabilis* GABA-gated chloride channel nucleic acid that do not encode for a *D. variabilis* GABA-gated chloride channel segment or are not found in SEQ. ID. NOs. 4, 5, 6 or the complement thereof. Such regions, if present, are preferably chosen to achieve a particular purposes. Examples of additional regions that can be used to achieve a particular purpose include capture regions that can be used as part of a sandwich assay, reporter regions that can be probed to indicate the presence of the nucleic acid, expression vector regions, and regions encoding for other polypeptides.

In different embodiments a *D. variabilis* GABA-gated chloride channel nucleic acid comprises or consists of a sequence that encodes a unique region of at least 9 contiguous amino acids, at least 18 contiguous amino acids, at least 27 contiguous amino acids, or at least 54 contiguous amino acids present in SEQ. ID. NOs. 1, 2, or 3; or comprises or consists of a sequence of at least 18 contiguous nucleotides, at least 36 contiguous nucleotides, or at least 72 contiguous nucleotides present in SEQ. ID. NOs. 4, 5, 6, or the complement thereof. Preferably, the *D. variabilis* GABA-gated chloride channel nucleic acid comprises or consists of the nucleotide sequence of SEQ. ID. NOs. 4, 5, or 6.

*D. variabilis* GABA-gated chloride channel nucleic acid also includes nucleic acid encoding a polypeptide having a sequence similarity of at least about 70%, at least about 80%, at least about 90%, or at least about 95% with SEQ. ID. NO. 1; and nucleic acid having a sequence similarity of at least about 85%, preferably 90%, with SEQ. ID. NO. 4. Sequence similarity for nucleic acid can be determined by the Smith and Waterman Bestfit Algorithm with gap weight 8; length weight 2; and FASTA (Pearson 1990. *Methods in Enzymology* 183, 63-98, hereby incorporated by reference herein). In one embodiment sequence similarity is determined using FASTA search program with the following parameters: MATRIX: BLOSUM50, GAP PENALTIES: open=−12; residue=−2.

The guidance provided in the present application can be used to obtain nucleic acid sequences encoding for *D. variabilis* GABA-gated chloride channels, for related channels from different sources and to construct channels having *D. variabilis* GABA-gated chloride channel activity. Obtaining nucleic acids encoding for channels from different sources, related to a *D. variabilis* GABA-gated chloride channel, is facilitated using sets of degenerative probes and primers and by the proper selection of hybridization conditions. Sets of degenerative probes and primers can be produced taking into account the degeneracy of the genetic code. Adjusting hybridization conditions is useful for controlling probe or primer specificity to allow for hybridization to nucleic acids having similar sequences.

Techniques employed for hybridization detection and PCR cloning are well known in the art. Nucleic acid detection techniques are described, for example, in Sambrook et al., in *Molecular Cloning, A Laboratory Manual*, 2$^{nd}$ Edition, Cold Spring Harbor Laboratory Press, 1989. PCR cloning techniques are described, for example, in White, *Methods in Molecular Cloning*, volume 67, Humana Press, 1997.

*D. variabilis* GABA-gated chloride channel probes and primers can be used to screen nucleic acid libraries containing, for example, genomic DNA or cDNA. Such libraries can be produced using techniques such as those described in Ausubel, *Current Protocols in Molecular Biology*, John Wiley, 1987-1998.

Starting with a particular *D. variabilis* GABA-gated chloride channel amino acid sequence and the known degeneracy of the genetic code, a large number of different encoding nucleic acid sequences can be obtained. The degeneracy of the genetic code arises because almost all amino acids are encoded for by different combinations of nucleotide triplets or "codons". The translation of a particular codon into a particular amino acid is well known in the art (see, e.g., Lewin *GENES IV*, p. 119, Oxford University Press, 1990). Amino acid are encoded for by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU.

Nucleic acid having a desired sequence can be synthesized using chemical and biochemical techniques. Examples of chemical techniques are described in Ausubel, *Current Protocols in Molecular Biology*, John Wiley, 1987-1998, and Sambrook et al., in *Molecular Cloning, A Laboratory Manual*, 2$^{nd}$ Edition, Cold Spring Harbor Laboratory Press, 1989.

Biochemical synthesis techniques involve the use of a nucleic acid template and appropriate enzymes such as DNA and/or RNA polymerases. Examples of such techniques include in vitro amplification techniques such as PCR and transcription based amplification, and in vivo nucleic acid replication. Examples of suitable techniques are provided by Ausubel, *Current Protocols in Molecular Biology*, John Wiley, 1987-1998, Sambrook et al., in *Molecular Cloning, A Laboratory Manual*, 2$^{nd}$ Edition, Cold Spring Harbor Laboratory Press, 1989, and Kacian et al., U.S. Pat. No. 5,480,784.

*D. Variabilis* GABA-Gated Chloride Channel Probes

A probe for a *D. variabilis* GABA-gated chloride channel nucleic acid contains a region that can specifically hybridize to *D. variabilis* GABA-gated chloride channel target nucleic acid under appropriate hybridization conditions and can distinguish *D. variabilis* GABA-gated chloride channel nucleic acid from non-target nucleic acids. Probes for *D. variabilis* GABA-gated chloride channel can contain nucleic acid that are not complementary to *D. variabilis* GABA-gated chloride channel nucleic acid.

Preferably, non-complementary nucleic acid that is present in a *D. variabilis* GABA-gated chloride channel nucleic acid probe has a particular purpose such as being a reporter sequence or being a capture sequence. However, additional nucleic acid need not have a particular purpose as long as the additional nucleic acid does not prevent the probe from distinguishing between target and non-target nucleic acid.

Hybridization occurs through complementary nucleotide bases. Hybridization conditions determine whether two molecules, or regions, have sufficiently strong interactions with each other to form a stable hybrid.

The degree of interaction between two molecules that hybridize together is reflected by the Tm of the produced hybrid. The higher the Tm the stronger the interaction and the more stable the hybrid. Tm is effected by different factors well known in the art such as the degree of complementarily, the type of complementary bases present (e.g., A-T hybridization versus G-C hybridization), the presence of modified nucleic acid, and solution components. (E.g., Sambrook et al., in *Molecular Cloning, A Laboratory Manual*, 2$^{nd}$ Edition, Cold Spring Harbor Laboratory Press, 1989.)

Stable hybrids are formed when the Tm of a hybrid is greater than the temperature employed under a particular set of hybridization assay conditions. The degree of specificity of a probe can be varied by adjusting the hybridization stringency conditions. Detecting probe hybridization is facilitated through the use of a detectable label. Examples of detectable labels include luminescent, enzymatic, and radioactive labels.

Examples of stringency conditions are provided in Sambrook et al., in *Molecular Cloning, A Laboratory Manual*, 2$^{nd}$ Edition, Cold Spring Harbor Laboratory Press, 1989. An example of high stringency conditions is as follows: Prehybridization of filters containing DNA is carried out for 2 hours to overnight at 65° C. in buffer composed of 6×SSC, 5× Denhardt's solution, and 100 µg/ml denatured salmon sperm DNA. Filters are hybridized for 12 to 48 hours at 65° C. in prehybridization mixture containing 100 µg/ml denatured salmon sperm DNA and 5-20×10$^6$ cpm of $^{32}$P-labeled probe. Washing of filters is done at 37° C. for 1 hour in a solution containing 2×SSC, 0.1% SDS. This is followed by a wash in 0.1×SSC, 0.1% SDS at 50° C. for 45 minutes. Other procedures using conditions of high stringency include, for example, either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Probes are composed of nucleic acids or derivatives thereof such as modified nucleic acid and peptide nucleic acid. Modified nucleic acid includes nucleic acid with one or more altered sugar groups, altered internucleotide linkages, and/or altered nucleotide purine or pyrimidine bases. References describing modified nucleic acid include WO 98/02582, U.S. Pat. No. 5,859,221 and U.S. Pat. No. 5,852, 188, each of which are hereby incorporated by reference herein.

Recombinant Expression

*D. variabilis* GABA-gated chloride channel polypeptides can be expressed from recombinant nucleic acid in a suitable host, or in a test tube using a translation system. Recombinantly expressed *D. variabilis* GABA-gated chloride channel polypeptides are preferably used in assays to screen for compounds that bind to the channel and modulate the activity of the channel.

Preferably, expression is achieved in a host cell using an expression vector. An expression vector contains recombinant nucleic acid encoding for a desired polypeptide along with regulatory elements for proper transcription and processing. The regulatory elements that may be present include those naturally associated with the recombinant nucleic acid and exogenous regulatory elements not naturally associated with the recombinant nucleic acid. Exogenous regulatory elements such as an exogenous promoter can be useful for expressing recombinant nucleic acid in a particular host.

Generally, the regulatory elements that are present in an expression vector include a transcriptional promoter, a ribosome binding site, a terminator, and an optionally present operator. A preferred element is a polyadenylation signal providing for processing in eukaryotic cells. Other preferred elements include an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

Expression vectors providing suitable levels of polypeptide expression in different hosts are well known in the art. Mammalian expression vectors well known in the art include pcDNA3 (Invitrogen), pMC1neo (Stratagene), pXT1 (Stratagene), pSG5 (Stratagene), EBO-pSV2-neo (ATCC 37593), pBPV-1(8-2) (ATCC 37110), pdBPV-MMT-neo(342-12) (ATCC 37224), pRSVgpt (ATCC 37199), pRS-Vneo (ATCC 37198), pSV2-dhfr (ATCC 37146), pUCTag (ATCC 37460), pCI-neo (Promega) and .lambda.ZD35 (ATCC 37565). Bacterial expression vectors well known in the art include pET11a (Novagen), lambda gt11 (Invitrogen), pcDNAII (Invitrogen), and pKK223-3 (Pharmacia). Fungal cell expression vectors well known in the art include pYES2 (Invitrogen) and Pichia expression vector (Invitrogen). Insect cell expression vectors well known in the art include Blue Bac III (Invitrogen).

Recombinant host cells may be prokaryotic or eukaryotic. Examples of recombinant host cells include the following: bacteria such as *E. coli*; fungal cells such as yeast; mammalian cells such as human, bovine, porcine, monkey and rodent; and insect cells such as Drosophila and silkworm derived cell lines. Commercially available mammalian cell lines include L cells L-M(TK.sup.-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

To enhance expression in a particular host it may be useful to modify the sequence provided in SEQ. ID. NOs. 4, 5, or 6 to take into account codon usage of the host. Codon usage of different organisms are well known in the art. (See, Ausubel, *Current Protocols in Molecular Biology*, John Wiley, 1987-1998, Supplement 33, Appendix 1C.)

Expression vectors may be introduced into host cells using standard techniques. Examples of such techniques include transformation, transfection, lipofection, protoplast fusion, and electroporation.

Nucleic acid encoding for a polypeptide can be expressed in a cell without the use of an expression vector employing, for example, synthetic mRNA or native mRNA. Additionally, mRNA can be translated in various cell-free systems such as wheat germ extracts and reticulocyte extracts, as well as in cell based systems, such as frog oocytes. Introduction of mRNA into cell based systems can be achieved, for example, by microinjection.

Antiparistic Applications

Using the present application as a guide compounds able to modulate *D. variabilis* GABA-gated chloride channel can be obtained and used to treat or prevent a *D. variabilis* infestation. Such compounds may also be useful in treating or preventing infestation of other parasites.

Compounds able to modulate *D. variabilis* GABA-gated chloride channel that are useful as an antiparasitic agent can be administered to a patient or can be used to treat a particular area to eliminate a parasite or prevent entry of a parasite.

A patient refers to a mammal being treated for the elimination or prevention of a *D. variabilis* infestation. Treatment can be carried out using different means including internal administration or topical administration.

Internal administration can be by different routes including oral or by injection to a patient. A tick can be exposed to internally administered compounds during blood feeding. Guidelines for pharmaceutical administration in general are provided in, for example, *Remington's Pharmaceutical Sciences* 18$^{th}$ Edition, Ed. Gennaro, Mack Publishing, 1990, and *Modern Pharmaceutics* 2$^{nd}$ Edition, Eds. Banker and Rhodes, Marcel Dekker, Inc., 1990, both of which are hereby incorporated by reference herein.

*D. variabilis* GABA-gated chloride channel active compounds having appropriate functional groups can be prepared as acidic or base salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

The compounds may also be administered to a patient by intravenous (both bolus and infusion), intraperitoneal, subcutaneous, topical with or without occlusion, or intramuscular form, all using forms well known to those of ordinary skill in the pharmaceutical arts. When administered by injection, the injectable solutions or suspensions may be formulated using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens for the antiparasitic applications of the present invention are selected taking into account factors well known in the art including type of mammal being treated as a patient, the age, weight, medical condition of the patient; the route of administration; the renal and hepatic function of the patient; and the particular compound employed. Optimal precision in achieving concentrations of drug within the range that yields efficacy without toxicity requires a regimen based on the kinetics of the drug's availability to target sites. This involves a consideration of the distribution, equilibrium, and elimination of the drug.

Topical application of antiparasitic compounds can be achieved through the use of a liquid drench or a shampoo containing an active compound as an aqueous solution, dispersion or suspension. These formulations generally contain a suspending agent such as bentonite, a wetting agent or the like excipient, and normally will also contain an antifoaming agent. In different embodiments of the present invention formulations contain from 0.001 to 1% by weight of the active ingredient, or contain from 0.01 to 1% by weight of the active compounds.

*D. variabilis* GABA-gated chloride channel modulating compounds can be provided in kit. Such a kit typically contains an active compound in dosage forms for use. A dosage form contains a sufficient amount of active compound such that a beneficial effect can be obtained when used during regular intervals, such as 1 to 6 times a day, during the course of 1 or more days. Preferably, a kit contains instructions indicating the use of the dosage form for treating or preventing a tick infestation and the amount of dosage form to be used over a specified time period.

EXAMPLES

Examples are provided below to further illustrate different features and advantages of the present invention. The examples also illustrate useful methodology for practicing the invention. These examples do not limit the claimed invention.

Example 1

Cloning of a *D. Variabilis* GABA-Gated Chloride Channel

A *D. variabilis* GABA-gated chloride channel was cloned using a *Rhipicephalus sanguineus* GluCl gene encoding segment as a probe (SEQ. ID. NO. 28) and screening a tick Dermacentor cDNA library. Cloned *D. variabilis* GABA-gated chloride channels were used to synthesize in vitro transcribed capped RNA.

A tick *Dermacentor* cDNA library was produced using PolyA$^+$ RNA purified from whole *Dermacentor* ticks to generate an oligo(dT)-primed ZAP cDNA library cloned as 5' EcoRI-3' XhoI inserts. The library consisted of approximately 1.8×10$^6$ independent clones prior to amplification. The ZAP Express cDNA Synthesis Kit and the ZAP Express™ cDNA GigapackIII Gold Cloning Kit were purchased from Stratagene (La Jolla, Calif.) and used according to the manufacturer's instructions.

The tick *Dermacentor* cDNA library was probed by detecting hybridization with the nucleic acid probe of SEQ. ID. NO. 28. Hybridization was performed in 6×SSPE, 0.1% SDS, 10× Denhardt's solution, salmon sperm DNA (200 µg/ml), and 45% formamide at 42° C. The membranes were then washed twice in i) 2×SSC, 0.5% SDS at room temperature for 15 minutes and ii) 0.2×SSC, 0.5% SDS at 42° C. for 30 minutes, followed by a single wash in 0.2×SSC, 0.5% SDS at 55° C. for 30 minutes. Nine positive clones, including Dv5, Dv8 and Dv9, were identified in the original screen.

The Dv5, Dv8 and Dv9 inserts were excised from the phage, converted to pBK-CMV phagemid vectors using the manufacturer's protocol (Stratagene, La Jolla, Calif.), and sequenced on an ABI PRISM™ 377 DNA Sequencer (Perkin Elmer, Foster City, Calif.). The open reading frames for Dv8, Dv9, and Dv5 are shown in SEQ. ID. NOs. 4,5, and 6.

Synthesis of In Vitro Transcribed Capped RNA

A PCR strategy was used to add the T7 promoter upstream of the initiating methionine (ATG) and a polyA+ tail following the stop codon (TAG) of the open reading frame (ORF) of clones Dv5, Dv8 and Dv9. Amplified ORFs containing the flanking T7 promoter and polyA+tail were used directly as templates in the in vitro transcription reaction (mMessage mMachine™, Ambion, Austin, Tex.).

After removal of DNA template, the volume was adjusted to 100 µl with nuclease free water, and RNA purified using a G-50 Sephadex Column (Boehringer Mannheim, Indianapolis, Ind.). The elutate was extracted with an equal volume of phenol/chloroform, followed with a second chloroform extraction, precipitated with isopropyl alcohol, and resuspended in nuclease-free water to a storage concentration of 1 µg/µl.

```
                                          SEQ. ID. NO. 28
CGGATATTGGACAGCATCATTGGCCAGGGTCGTTATGACTGCAGGATCCG

GCCCATGGGAATTAACAACACAGACGGGCCGGCTCTTGTACGCGTTAACA

TCTTTGTAAGAAGTATCGGCAGAATTGATGACGTCACCATGGAGTACACA

GTGCAAATGACGTTCAGAGAGCAGTGGCGGGACGAGAGACTCCAGTACGA
```

-continued

```
CGACTTGGGCGGCCAGGTTCGCTACCTGACGCTCACCGAACCGGACAAGC
TTTGGAAGCCGGACCTGTTTTTCTCCAACGAGAAAGAGGGACACTTCCAC
AACATCATCATGCCCAACGTGCTTCTACGCATACATCCCAACGGCGACGT
TCTCTTCAGCATCAGAATATCCTTGGTGCTTTCATGTCCGATGAACCTGA
AATTTTATCCTTTGGATAAACAAATCTGCTCTATCGTCATGGTGAGCTAT
GGGTATACAACAGAGGACCTGGTGTTTCTATGGAAAGAGGGGGATCCTGT
ACAGGTCACAAAAAATCTCCACTTGCCACGTTTCACGCTGGAAAGGTTTC
AAACCGACTACTGCACCAGTCGGACCAACACTGGCGAGTACAGCTGCTTG
CGCGTGGACCTGGTGTTCAAGCGCGAGTTCAGCTACTACCTGATCCAGAT
CTACATCCCGTGCTGCATGCTGGTCATCGTGTCCTGGGTGTCGTTCTGGC
TCGACCCCACCTCGATCCCGGCGCGAGTGTCGCTGGGCGTCACCACCCTG
CTCACCATGGCCACGCAGATATCGGGCATCAACGCCTCGCTGCCTCCCGT
TTCCTACACCAAGGCCATTGACGTGTGGACCGGCGTCTGTCTGACCTTCG
TATTCGGCGCGCTCCTCGAGTTCGCCCTGGTCAACTACGCCTCGCGGTCA
GATTCACGCCGGCAGAACATGCAGAAGCAGAAGCAGAGGAAATGGGAGCT
CGAGCCGCCCCTGGACTCGGACCACCTGGAGGACGGCGCCACCACGTTCG
CCATGAGGCCGCTGGTGCACCACCACGGAGAGCTGCATGCCGACAAGTTG
CGGCAGTGCGAAGTCCACATGAAGACCCCCAAGACGAACCTTTGCAAGGC
CTGGCTTTCCAGGTTTCCCACGCGATCCAAACGCATCGACGTCGTCTCGC
GGATCTTCTTTCCGCTCATGTTCGCCCTCTTCAACCTCGTCTACTGG
```

Example 2

SEQ. ID. NOs. 1-6

SEQ. ID. NOs. 1-6 provide amino acid and nucleic acid sequences for *D. variabilis* GABA-gated chloride channels. As noted above, the differences between the amino acid sequences of SEQ. ID. NOs. 1-3, and differences between SEQ. ID. NOs. 4-6, are due to mRNA editing and strain variation.

```
                                SEQ. ID. NO. 1 (from Dv8)
MRQAMAFSCWSFVLFVAVAVTSAGRDNGPAPLRPGQTQRGQNITQILNAF
FTRGYDRRVRPNYGGVPVEVGVTMQIISISTVSEVQMDFTSDFYFRQSWR
DERLSFQKSPDLESMTVGAEVAERIWVPDTFFANEKSAYFHAATTPNTFL
RIGSGGEVFRSIRLTVTASCPMDLRYFPMDRQACTIEIESFGYTMKDIRY
RWSDGDTSVRIAKEVELPQFKVLGHVQKAKEVALTTGNYSRLVCEIRFAR
SMGYYLIQIYIPAGLIVVISWVSFWLHRDASPARVALGVTTVLTMTTLMS
STNAALPKISYVKSIDVYLGTCFVMVFTALLEYAAVGYLGKRITMRKTRC
QQLAKLAEQHRQRCAAASSNEPSSEPLLASPEVSIVKTVGSCQVCPAAVA
SQGQPREAPPTGFTMGRRGADQCCPGLQGSCQVCPAAVASQTQQQAPPPG
IPMEVRLKMVDPKGFSKSSTLENTVNGAPDIEAAFCKNPNKLFGVGPSDI
DKYSRVVFPVCFVCFDLMYWIIYLHISDVLPDDVGDD
```

```
                                SEQ. ID. NO.2 (from Dv9)
MRQAMAFSCWSFVLFVAVAVTSAGRDNGPAPLRPGQTQRGQNITQILNAF
FTRGYDRRVRPNYGGVPVEVGVTMQIISISTVSEVQMDFTSDFYFRQSWR
DERLSFQKSPDLESMTVGAEVAERIWVPDTFFANEKSAYFHAATTPNTFL
RIGSGGEVFRSIRLTVTASCPMDLRYFPMDRQACTIEIESFGYTMKDIRY
RWSDGDTSVRIAKEVELPQFKVLGHVQKAKEVALTTGNYSRLVCEIRFAR
SMGYYLIQIYIPAGLIVVISWVSFWLHRNASPARVALGVTTVLTMTTLMS
STNAALPKISYVKSIDVYLGTCFVMVFTALLEYAAVGYLGKRITMRKTRC
QQLAKLAEQHRQRCAAASSNEPSSEPLLASPEVSIVKTVGSCQVCPAAVA
SQGQPREAPPTGFTMGRRGADQCCPGLQGSCQVCPAAVASQTQQQAPPPG
IPMEVRLKMVDPKGFSKSSTLENTVNGAPDIEAAFCKNPNKLFGVGPSDI
DKYSRVVFPVCFVCFDLMYWIIYLHISDVLPDDVGDD
```

```
                                SEQ. ID. NO. 3 (from Dv5)
MRQAMAFSCWSFVLFVAVAVTSAGRDNGPAPLRPGQTQRGQNITQILNAF
FTRGYDRRVRPNYGGVPVEVGVTMQIISISTVSEVQMDFTSDFYFRQSWR
DERLSFQKSPDLESMTVGAEVAERIWVPDTFFANEKSAYFHAATTPNTFL
RIGSGGEVFRSIRLTVTAGCPMDLRYFPMDRQACTIEIESFGYTMKDIRY
RWSDGDTSVRIAKEVELPQFKVLGHVQKAKEVALTTGNYSRLVCEIRFAR
SMGYYLIQIYIPAGLIVVISWVSFWLHRDASPARVALGVTTVLTMTTLMS
STNAALPKISYVKSIDVYLGTCFVMVFTALLEYAAVGYLGKRITMRKTRC
QQLAKLAEQHRQRCAAASSNEPSSEPLLASPEVSIVKTVGSCRVCPAAVA
SQGQPREAPPTGFTMGRRGADQCCPGLQGSCQVCPAAVASQTQQQAPPPG
IPMEVRLKMVDPKGFSKSSTLENTVNGAPGIEAAFCKNPNKLFGVGPSDI
DKYSRVVFPVCFVCFGLMYWIIYLHVSDVLPDDVGDD
```

```
                                SEQ. ID. NO.4 (from Dv8)
ATGAGACAAGCGATGGCGTTCAGTTGCTGGTCCTTCGTTCTCTTCGTGGC
CGTCGCTGTCACCAGTGCCGGTCGGGATAATGGTCCAGCCCCCCTGCGGC
CGGGACAAACGCAACGTGGACAAAACATCACGCAGATTCTGAATGCCTTC
TTTACACGTGGGTACGACAGGAGGGTGAGGCCAAATTATGGCGGCGTTCC
AGTGGAAGTTGGCGTCACTATGCAGATTATCAGCATAAGTACAGTCTCTG
AAGTACAAATGGACTTTACTTCTGACTTCTATTTCCGGCAATCGTGGCGG
GACGAGCGACTCTCGTTCCAGAAAAGCCCAGACCTCGAGAGCATGACTGT
GGGCGCTGAAGTGGCCGAGAGGATCTGGGTACCCGACACCTTCTTCGCCA
ACGAGAAGAGCGCCTACTTTCATGCGGCCACAACGCCCAACACTTTCCTC
CGCATCGGCTCCGGAGGAGAGGTTTTCCGCAGTATTCGACTGACGGTGAC
TGCCAGCTGCCCAATGGATCTCAGATACTTCCCGATGGACAGACAAGCGT
GCACTATAGAGATAGAAAGCTTTGGTTATACCATGAAAGACATCCGCTAC
CGGTGGTCGGACGGTGACACCTCCGTCCGCATCGCCAAGGAGGTAGAGTT
GCCGCAGTTCAAGGTCCTCGGTCACGTCCAAAAAGCCAAAGAGGTTGCCC
TAACGACAGGAAACTACTCCCGCCTGGTATGTGAAATACGGTTCGCCCGC
TCCATGGGCTACTACCTGATCCAGATCTACATCCCGGCCGGATTGATCGT
GGTTATTTCCTGGGTCTCCTTTTGGCTCCACCGTGACGCTAGTCCAGCTC
```

-continued

GCGTCGCGCTCGGCGTCACCACCGTGCTCACGATGACCACACTCATGTCC

AGTACCAACGCAGCGCTGCCCAAAATATCCTACGTCAAGAGTATCGACGT

CTACCTGGGCACATGTTTCGTAATGGTGTTTACCGCGCTCCTGGAGTACG

CCGCGGTAGGATATCTCGGCAAGAGAATCACCATGAGGAAAACCCGCTGT

CAGCAGCTGGCAAAACTTGCAGAGCAACACAGGCAGAGATGCGCCGCGGC

TTCTTCCAACGAGCCAAGCTCTGAGCCCTTGCTAGCCAGTCCTGAAGTAT

CCATTGTCAAGACGGTCGGTTCCTGTCAAGTTTGTCCTGCTGCGGTGGCA

TCCCAAGGACAACCGAGGGAAGCACCACCAACCGGATTTACCATGGGTCG

CAGAGGCGCAGACCAATGTTGCCCTGGTCTCCAGGGTTCATGTCAGGTCT

GCCCCGCTGCGGTCGCCTCACAAACCCAACAACAGGCTCCTCCACCAGGG

ATACCTATGGAAGTACGTCTCAAAATGGTTGACCCCAAGGGATTCAGCAA

ATCCTCGACTCTGGAGAACACCGTCAACGGCGCGCCGGACATCGAGGCAG

CGTTTTGCAAGAACCCCAACAAATTATTTGGCGTCGGCCCTTCCGATATC

GACAAGTACTCCCGAGTGGTGTTCCCCGTTTGCTTCGTCTGTTTCGACCT

CATGTACTGGATCATTTACCTGCACATCAGCGACGTTCTGCCGGACGACG

TCGGCGACGACTAG

SEQ. ID. NO. 5 (from Dv9)

ATGAGACAAGCGATGGCGTTCAGTTGCTGGTCCTTCGTTCTCTTCGTGGC

CGTCGCTGTCACCAGTGCCGGTCGGGATAATGGTCCAGCCCCCCTGCGGC

CGGGACAAACGCAACGTGGACAAAACATCACGCAGATTCTGAATGCCTTC

TTTACACGTGGGTACGACAGGAGGGTGAGGCCAAATTATGGCGGCGTTCC

AGTGGAAGTTGGCGTCACTATGCAGATTATCAGCATAAGTACAGTCTCTG

AAGTACAAATGGACTTTACTTCTGACTTCTATTTCCGGCAATCGTGGCGG

GACGAGCGACTCTCGTTCCAGAAAAGCCCAGACCTCGAGAGCATGACTGT

GGGCGCTGAAGTGGCCGAGAGGATCTGGGTACCCGACACCTTCTTCGCCA

ACGAGAAGAGCGCCTACTTTCATGCGGCCACAACGCCCAACACTTTCCTC

CGCATCGGCTCCGGAGGAGAGGTTTTCCGCAGTATTCGACTGACGGTGAC

TGCCAGCTGCCCAATGGATCTCAGATACTTCCCGATGGACAGACAAGCGT

GCACTATAGAGATAGAAAGCTTTGGTTATACCATGAAAGACATCCGCTAC

CGGTGGTCGGACGGTGACACGTCCGTCCGCATCGCCAAGGAGGTAGAGTT

GCCGCAGTTCAAGGTCCTCGGTCACGTCCAAAAAGCCAAAGAGGTTGCCC

TAACGACAGGAAACTACTCCCGCCTGGTATGTGAAATACGGTTCGCCCGC

TCCATGGGCTACTACCTGATCCAGATCTACATCCCGGCCGGATTGATCGT

GGTTATTTCCTGGGTCTCCTTTTGGCTCCACCGTAACGCTAGTCCAGCTC

GCGTCGCGCTCGGCGTCACCACCGTGCTCACGATGACCACACTCATGTCC

AGTACCAACGCAGCGCTGCCCAAAATATCCTACGTCAAGAGTATCGACGT

CTACCTGGGCACATGTTTCGTAATGGTGTTTACCGCGCTCCTGGAGTACG

CCGCGGTAGGATATCTCGGCAAGAGAATCACCATGAGGAAAACCCGCTGT

CAGCAGCTGGCAAAACTTGCAGAGCAACACAGGCAGAGATGCGCCGCAGC

TTCTTCCAACGAGCCAAGCTCTGAGCCCTTGCTAGCCAGTCCTGAAGTAT

CCATTGTCAAGACGGTCGGTTCCTGTCAAGTTTGTCCTGCTGCGGTGGCA

TCCCAAGGACAACCGAGGGAAGCACCACCAACCGGATTTACCATGGGTCG

CAGAGGCGCAGACCAATGTTGCCCTGGTCTCCAGGGTTCATGTCAGGTCT

GCCCCGCTGCGGTCGCCTCACAAACCCAACAACAGGCTCCTCCACCAGGG

ATACCTATGGAAGTACGTCTCAAAATGGTTGACCCCAAGGGATTCAGCAA

ATCCTCGACTCTGGAGAACACCGTCAACGGCGCGCCGGACATCGAGGCAG

CGTTTTGCAAGAACCCCAACAAATTATTTGGCGTCGGCCCTTCCGATATC

GACAAGTACTCCCGAGTGGTGTTCCCCGTTTGCTTCGTCTGTTTCGACCT

CATGTACTGGATCATTTACCTGCACATCAGCGACGTTCTGCCGGACGACG

TCGGCGACGACTAG

SEQ. ID. NO. 6 (from Dv5)

ATGAGACAAGCGATGGCGTTCAGTTGCTGGTCCTTCGTTCTCTTCGTGGC

CGTCGCTGTCACCAGTGCCGGTCGGGATAATGGTCCAGCCCCCCTGCGGC

CGGGACAAACGCAACGTGGACAAAACATCACGCAGATTCTGAATGCCTTC

TTTACACGTGGGTACGACAGGAGGGTGAGGCCAAATTATGGCGGCGTTCC

AGTGGAAGTTGGCGTCACTATGCAGATTATCAGCATAAGTACAGTCTCTG

AAGTACAAATGGACTTTACTTCTGACTTCTATTTCCGGCAATCGTGGCGG

GACGAGCGACTCTCGTTCCAGAAAAGCCCAGACCTCGAGAGCATGACTGT

GGGCGCTGAAGTGGCCGAGAGGATCTGGGTACCCGACACCTTCTTCGCCA

ACGAGAAGAGCGCCTACTTTCATGCGGCCACAACGCCCAACACTTTCCTC

CGCATCGGCTCCGGAGGAGAGGTTTTCCGCAGTATTCGACTGACGGTGAC

TGCCGGCTGCCCAATGGATCTCAGATACTTCCCGATGGACAGACAAGCGT

GCACTATAGAGATAGAAAGCTTTGGTTATACCATGAAAGACATCCGCTAC

CGGTGGTCGGACGGTGACACCTCCGTCCGCATCGCCAAGGAGGTAGAGTT

GCCGCAGTTCAAGGTCCTCGGTCACGTCCAAAAAGCCAAAGAGGTTGCCC

TAACGACAGGAAACTACTCCCGCCTGGTATGTGAAATACGGTTCGCCCGC

TCCATGGGCTACTACCTGATCCAGATCTACATCCCGGCCGGATTGATCGT

GGTTATTTCCTGGGTCTCCTTTTGGCTCCACCGTGACGCTAGTCCAGCTC

GCGTCGCGCTCGGCGTCACCACCGTGCTCACGATGACCACACTCATGTCC

AGTACCAACGCAGCGCTGCCCAAAATATCCTACGTCAAGAGTATCGACGT

CTACCTGGGCACATGTTTCGTAATGGTGTTTACCGCGCTCCTGGAGTACG

CCGCGGTAGGATATCTCGGCAAGAGAATCACCATGAGGAAAACCCGCTGT

CAGCAGCTGGCAAAACTTGCAGAGCAACACAGGCAGAGATGCGCCGCGGC

TTCTTCCAACGAGCCAAGCTCTGAGCCCTTGCTAGCCAGTCCTGAGGTAT

CCATTGTCAAGACGGTCGGTTCCTGTCGGGTTTGTCCTGCTGCGGTGGCA

TCCCAAGGACAACCGAGGGAAGCACCACCAACCGGATTTACCATGGGTCG

CAGAGGCGCAGACCAATGTTGCCCTGGTCTCCAGGGTTCATGTCAGGTCT

GCCCCGCTGCGGTCGCCTCACAAACCCAACAACAGGCTCCTCCACCAGGG

ATACCTATGGAAGTACGTCTCAAAATGGTTGACCCCAAGGGATTCAGCAA

ATCCTCGACTCTGGAGAACACCGTCAACGGCGCGCCGGGCATCGAGGCAG

CGTTTTGCAAGAACCCCAACAAATTATTTGGCGTCGGCCCTTCCGATATCG

-continued

```
ACAAGTACTCCCGAGTGGTGTTCCCCGTTTGCTTCGTCTGTTTCGGCCTC

ATGTACTGGATCATTTACCTGCACGTCAGCGACGTTCTGCCGGACGACGT

CGGCGACGACTAG
```

Example 3

Functional Expression

Functional expression of a *D. variabilis* GABA-gated chloride channel was observed using MRNA encoding for the polypeptide of SEQ. ID. NOs. 1, 2, and 3 injected into *Xenopus laevis* oocytes. MRNA encoding for SEQ. ID. NOs. 1, 2, and 3 were obtained using the Dv8, Dv9, and Dv5 clones as described in Example 1.

*Xenopus laevis* oocytes were prepared and injected using standard methods previously described. (Arena et al., *Mol. Pharmaco.* 40:368-374, 1991; and Arena et al., *Mol. Brain Res.* 15:339-348, 1992.) Adult female *Xenopus laevis* were anesthetized with 0.17% tricaine methanesulfonate and the ovaries were surgically removed and placed in a solution consisting of (mM): NaCl 82.5, KCl 2, $MgCl_2$ 1, HEPES 5, NaPyruvate 2.5, Penicillin G. 100,000 units/L, Streptomycin Sulfate 1000 mg/L, pH 7.5 (Mod. OR-2).

Ovarian lobes were broken open, rinsed several times in Mod. OR-2, and incubated in 0.2% collagenase (Sigma, Type1) in Mod. OR-2 at room temperature with gentle shaking. After 1 hour the collagenase solution was renewed and the oocytes were incubated for an additional 30-90 minutes until approximately 50% of the oocytes were released from the ovaries. Stage V and VI oocytes were selected and placed in media containing (mM): NaCl 96, KCl 2, $MgCl_2$ 1, $CaCl_2$ 1.8, HEPES 5, NaPyruvate 2.5, theophylline 0.5, gentamicin 50 mg/ml, pH 7.5 (ND-96) for 16-24 hours before injection. Oocytes were injected with 50 nl of Dv8, Dv9, or Dv5 RNA at a concentration of 0.2 mg/ml. Oocytes were incubated at 18° C. for 1-6 days in ND-96 before recording.

Recordings were made at room temperature in modified ND-96 consisting of (mM): NaCl 96, $MgCl_2$ 1, $CaCl_2$ 0.1, $BaCl_2$ 3.5, HEPES 5, pH 7.5. Oocytes were voltage clamped using a Dagan CA1 two microelectrode amplifier (Dagan Corporation, Minneapolis, Minn.) interfaced to a Macintosh 7100/80 computer. The current passing electrode was filled with 0.7 M KCl, 1.7 M KCitrate, and the voltage recording electrode was filled with 1 M KCl. Throughout the experiment oocytes were superfused with modified ND-96 (control solution) or with ND-96 containing potential channel activators and blockers at a rate of approximately 3 ml/min. Data were acquired at 100 Hz and filtered at 33.3 Hz using Pulse software from HEKA Elektronik (Lambrecht, Germany). All recordings were performed from a holding potential of either 0 or −30 mV.

Oocytes expressing Dv8 and Dv9 exhibited a rapidly activating current in response to application of 1 mM GABA (FIGS. 4 and 5). During a 60s application of GABA approximately 50% of the current desensitized and the remaining current deactivated rapidly upon wash-out of GABA. Repeated applications of 1 mM GABA elicited similar responses. In contrast, 1 mM glutamate did not activate a current. The GABA-activated current was blocked completely by 5 μM fipronil (FIG. 5) and by 10 μM picrotoxinin (data not shown). Oocytes injected with Dv5 mRNA responded similarly to oocytes injected with Dv8 and Dv9 mRNA (data not shown).

Other embodiments are within the following claims. While several embodiments have been shown and described, various modifications may be made without departing from the spirit and scope of the present invention.

---

What is claimed is:

1. A purified polypeptide, wherein said polypeptide comprises an amino acid sequence selected from the group consisting of SEQ. ID. NO. 1, SEQ. ID. NO. 2, and SEQ. ID. NO. 3.

2. The polypeptide of claim 1, wherein said polypeptide consists of an amino acid sequence selected from the group consisting of SEQ. ID. NO. 1, SEQ. ID. NO. 2, and SEQ. ID. NO. 3.

* * * * *

SEQUENCE LISTING

```
<160> NUMBER OF SEQ ID NOS: 28

<210> SEQ ID NO 1
<211> LENGTH: 537
<212> TYPE: PRT
<213> ORGANISM: Dermacentor variabilis

<400> SEQUENCE: 1

Met Arg Gln Ala Met Ala Phe Ser Cys Trp Ser Phe Val Leu Phe Val
 1               5                  10                  15

Ala Val Ala Val Thr Ser Ala Gly Arg Asp Asn Gly Pro Ala Pro Leu
            20                  25                  30

Arg Pro Gly Gln Thr Gln Arg Gly Gln Asn Ile Thr Gln Ile Leu Asn
        35                  40                  45

Ala Phe Phe Thr Arg Gly Tyr Asp Arg Arg Val Arg Pro Asn Tyr Gly
    50                  55                  60

Gly Val Pro Val Glu Val Gly Val Thr Met Gln Ile Ile Ser Ile Ser
65                  70                  75                  80

Thr Val Ser Glu Val Gln Met Asp Phe Thr Ser Asp Phe Tyr Phe Arg
                85                  90                  95
```

-continued

```
Gln Ser Trp Arg Asp Glu Arg Leu Ser Phe Gln Lys Ser Pro Asp Leu
            100                 105                 110

Glu Ser Met Thr Val Gly Ala Glu Val Ala Glu Arg Ile Trp Val Pro
        115                 120                 125

Asp Thr Phe Phe Ala Asn Glu Lys Ser Ala Tyr Phe His Ala Ala Thr
    130                 135                 140

Thr Pro Asn Thr Phe Leu Arg Ile Gly Ser Gly Gly Glu Val Phe Arg
145                 150                 155                 160

Ser Ile Arg Leu Thr Val Thr Ala Ser Cys Pro Met Asp Leu Arg Tyr
                165                 170                 175

Phe Pro Met Asp Arg Gln Ala Cys Thr Ile Glu Ile Glu Ser Phe Gly
            180                 185                 190

Tyr Thr Met Lys Asp Ile Arg Tyr Arg Trp Ser Asp Gly Asp Thr Ser
        195                 200                 205

Val Arg Ile Ala Lys Glu Val Glu Leu Pro Gln Phe Lys Val Leu Gly
    210                 215                 220

His Val Gln Lys Ala Lys Glu Val Ala Leu Thr Thr Gly Asn Tyr Ser
225                 230                 235                 240

Arg Leu Val Cys Glu Ile Arg Phe Ala Arg Ser Met Gly Tyr Tyr Leu
                245                 250                 255

Ile Gln Ile Tyr Ile Pro Ala Gly Leu Ile Val Val Ile Ser Trp Val
            260                 265                 270

Ser Phe Trp Leu His Arg Asp Ala Ser Pro Ala Arg Val Ala Leu Gly
        275                 280                 285

Val Thr Thr Val Leu Thr Met Thr Thr Leu Met Ser Ser Thr Asn Ala
    290                 295                 300

Ala Leu Pro Lys Ile Ser Tyr Val Lys Ser Ile Asp Val Tyr Leu Gly
305                 310                 315                 320

Thr Cys Phe Val Met Val Phe Thr Ala Leu Leu Glu Tyr Ala Ala Val
                325                 330                 335

Gly Tyr Leu Gly Lys Arg Ile Thr Met Arg Lys Thr Arg Cys Gln Gln
            340                 345                 350

Leu Ala Lys Leu Ala Glu Gln His Arg Gln Arg Cys Ala Ala Ala Ser
        355                 360                 365

Ser Asn Glu Pro Ser Ser Glu Pro Leu Leu Ala Ser Pro Glu Val Ser
    370                 375                 380

Ile Val Lys Thr Val Gly Ser Cys Gln Val Cys Pro Ala Ala Val Ala
385                 390                 395                 400

Ser Gln Gly Gln Pro Arg Glu Ala Pro Thr Gly Phe Thr Met Gly
                405                 410                 415

Arg Arg Gly Ala Asp Gln Cys Cys Pro Gly Leu Gln Gly Ser Cys Gln
            420                 425                 430

Val Cys Pro Ala Ala Val Ala Ser Gln Thr Gln Gln Ala Pro Pro
        435                 440                 445

Pro Gly Ile Pro Met Glu Val Arg Leu Lys Met Val Asp Pro Lys Gly
    450                 455                 460

Phe Ser Lys Ser Ser Thr Leu Glu Asn Thr Val Asn Gly Ala Pro Asp
465                 470                 475                 480

Ile Glu Ala Ala Phe Cys Lys Asn Pro Asn Lys Leu Phe Gly Val Gly
                485                 490                 495

Pro Ser Asp Ile Asp Lys Tyr Ser Arg Val Val Phe Pro Val Cys Phe
            500                 505                 510

Val Cys Phe Asp Leu Met Tyr Trp Ile Ile Tyr Leu His Ile Ser Asp
```

```
                515                 520                 525
Val Leu Pro Asp Asp Val Gly Asp Asp
    530                 535

<210> SEQ ID NO 2
<211> LENGTH: 537
<212> TYPE: PRT
<213> ORGANISM: Dermacentor variabilis

<400> SEQUENCE: 2

Met Arg Gln Ala Met Ala Phe Ser Cys Trp Ser Phe Val Leu Phe Val
 1               5                  10                  15

Ala Val Ala Val Thr Ser Ala Gly Arg Asp Asn Gly Pro Ala Pro Leu
            20                  25                  30

Arg Pro Gly Gln Thr Gln Arg Gly Gln Asn Ile Thr Gln Ile Leu Asn
        35                  40                  45

Ala Phe Phe Thr Arg Gly Tyr Asp Arg Arg Val Arg Pro Asn Tyr Gly
    50                  55                  60

Gly Val Pro Val Glu Val Gly Val Thr Met Gln Ile Ile Ser Ile Ser
65                  70                  75                  80

Thr Val Ser Glu Val Gln Met Asp Phe Thr Ser Asp Phe Tyr Phe Arg
                85                  90                  95

Gln Ser Trp Arg Asp Glu Arg Leu Ser Phe Gln Lys Ser Pro Asp Leu
            100                 105                 110

Glu Ser Met Thr Val Gly Ala Glu Val Ala Glu Arg Ile Trp Val Pro
        115                 120                 125

Asp Thr Phe Phe Ala Asn Glu Lys Ser Ala Tyr Phe His Ala Ala Thr
    130                 135                 140

Thr Pro Asn Thr Phe Leu Arg Ile Gly Ser Gly Gly Glu Val Phe Arg
145                 150                 155                 160

Ser Ile Arg Leu Thr Val Thr Ala Ser Cys Pro Met Asp Leu Arg Tyr
                165                 170                 175

Phe Pro Met Asp Arg Gln Ala Cys Thr Ile Glu Ile Glu Ser Phe Gly
            180                 185                 190

Tyr Thr Met Lys Asp Ile Arg Tyr Arg Trp Ser Asp Gly Asp Thr Ser
        195                 200                 205

Val Arg Ile Ala Lys Glu Val Glu Leu Pro Gln Phe Lys Val Leu Gly
    210                 215                 220

His Val Gln Lys Ala Lys Glu Val Ala Leu Thr Thr Gly Asn Tyr Ser
225                 230                 235                 240

Arg Leu Val Cys Glu Ile Arg Phe Ala Arg Ser Met Gly Tyr Tyr Leu
                245                 250                 255

Ile Gln Ile Tyr Ile Pro Ala Gly Leu Ile Val Ile Ser Trp Val
            260                 265                 270

Ser Phe Trp Leu His Arg Asn Ala Ser Pro Ala Arg Val Ala Leu Gly
        275                 280                 285

Val Thr Thr Val Leu Thr Met Thr Thr Leu Met Ser Ser Thr Asn Ala
    290                 295                 300

Ala Leu Pro Lys Ile Ser Tyr Val Lys Ser Ile Asp Val Tyr Leu Gly
305                 310                 315                 320

Thr Cys Phe Val Met Val Phe Thr Ala Leu Leu Glu Tyr Ala Ala Val
                325                 330                 335

Gly Tyr Leu Gly Lys Arg Ile Thr Met Arg Lys Thr Arg Cys Gln Gln
            340                 345                 350
```

-continued

```
Leu Ala Lys Leu Ala Glu Gln His Arg Gln Arg Cys Ala Ala Ala Ser
        355                 360                 365
Ser Asn Glu Pro Ser Ser Glu Pro Leu Leu Ala Ser Pro Glu Val Ser
    370                 375                 380
Ile Val Lys Thr Val Gly Ser Cys Gln Val Cys Pro Ala Ala Val Ala
385                 390                 395                 400
Ser Gln Gly Gln Pro Arg Glu Ala Pro Pro Thr Gly Phe Thr Met Gly
                405                 410                 415
Arg Arg Gly Ala Asp Gln Cys Cys Pro Gly Leu Gln Gly Ser Cys Gln
            420                 425                 430
Val Cys Pro Ala Ala Val Ala Ser Gln Thr Gln Gln Ala Pro Pro
        435                 440                 445
Pro Gly Ile Pro Met Glu Val Arg Leu Lys Met Val Asp Pro Lys Gly
    450                 455                 460
Phe Ser Lys Ser Ser Thr Leu Glu Asn Thr Val Asn Gly Ala Pro Asp
465                 470                 475                 480
Ile Glu Ala Ala Phe Cys Lys Asn Pro Asn Lys Leu Phe Gly Val Gly
                485                 490                 495
Pro Ser Asp Ile Asp Lys Tyr Ser Arg Val Val Phe Pro Val Cys Phe
            500                 505                 510
Val Cys Phe Asp Leu Met Tyr Trp Ile Ile Tyr Leu His Ile Ser Asp
        515                 520                 525
Val Leu Pro Asp Asp Val Gly Asp Asp
    530                 535

<210> SEQ ID NO 3
<211> LENGTH: 537
<212> TYPE: PRT
<213> ORGANISM: Dermacentor variabilis

<400> SEQUENCE: 3

Met Arg Gln Ala Met Ala Phe Ser Cys Trp Ser Phe Val Leu Phe Val
 1               5                  10                  15
Ala Val Ala Val Thr Ser Ala Gly Arg Asp Asn Gly Pro Ala Pro Leu
            20                  25                  30
Arg Pro Gly Gln Thr Gln Arg Gly Gln Asn Ile Thr Gln Ile Leu Asn
        35                  40                  45
Ala Phe Phe Thr Arg Gly Tyr Asp Arg Arg Val Arg Pro Asn Tyr Gly
    50                  55                  60
Gly Val Pro Val Glu Val Gly Val Thr Met Gln Ile Ile Ser Ile Ser
65                  70                  75                  80
Thr Val Ser Glu Val Gln Met Asp Phe Thr Ser Asp Phe Tyr Phe Arg
                85                  90                  95
Gln Ser Trp Arg Asp Glu Arg Leu Ser Phe Gln Lys Ser Pro Asp Leu
            100                 105                 110
Glu Ser Met Thr Val Gly Ala Glu Val Ala Glu Arg Ile Trp Val Pro
        115                 120                 125
Asp Thr Phe Phe Ala Asn Glu Lys Ser Ala Tyr Phe His Ala Ala Thr
    130                 135                 140
Thr Pro Asn Thr Phe Leu Arg Ile Gly Ser Gly Gly Glu Val Phe Arg
145                 150                 155                 160
Ser Ile Arg Leu Thr Val Thr Ala Gly Cys Pro Met Asp Leu Arg Tyr
                165                 170                 175
Phe Pro Met Asp Arg Gln Ala Cys Thr Ile Glu Ile Glu Ser Phe Gly
            180                 185                 190
```

```
Tyr Thr Met Lys Asp Ile Arg Tyr Arg Trp Ser Asp Gly Asp Thr Ser
        195                 200                 205

Val Arg Ile Ala Lys Glu Val Glu Leu Pro Gln Phe Lys Val Leu Gly
        210                 215                 220

His Val Gln Lys Ala Lys Glu Val Ala Leu Thr Thr Gly Asn Tyr Ser
225                 230                 235                 240

Arg Leu Val Cys Glu Ile Arg Phe Ala Arg Ser Met Gly Tyr Tyr Leu
                245                 250                 255

Ile Gln Ile Tyr Ile Pro Ala Gly Leu Ile Val Ile Ser Trp Val
                260                 265                 270

Ser Phe Trp Leu His Arg Asp Ala Ser Pro Ala Arg Val Ala Leu Gly
        275                 280                 285

Val Thr Thr Val Leu Thr Met Thr Thr Leu Met Ser Ser Thr Asn Ala
        290                 295                 300

Ala Leu Pro Lys Ile Ser Tyr Val Lys Ser Ile Asp Val Tyr Leu Gly
305                 310                 315                 320

Thr Cys Phe Val Met Val Phe Thr Ala Leu Leu Glu Tyr Ala Ala Val
                325                 330                 335

Gly Tyr Leu Gly Lys Arg Ile Thr Met Arg Lys Thr Arg Cys Gln Gln
                340                 345                 350

Leu Ala Lys Leu Ala Glu Gln His Arg Gln Arg Cys Ala Ala Ala Ser
            355                 360                 365

Ser Asn Glu Pro Ser Ser Glu Pro Leu Leu Ala Ser Pro Glu Val Ser
        370                 375                 380

Ile Val Lys Thr Val Gly Ser Cys Arg Val Cys Pro Ala Ala Val Ala
385                 390                 395                 400

Ser Gln Gly Gln Pro Arg Glu Ala Pro Thr Gly Phe Thr Met Gly
                405                 410                 415

Arg Arg Gly Ala Asp Gln Cys Cys Pro Gly Leu Gln Gly Ser Cys Gln
            420                 425                 430

Val Cys Pro Ala Ala Val Ala Ser Gln Thr Gln Gln Ala Pro Pro
        435                 440                 445

Pro Gly Ile Pro Met Glu Val Arg Leu Lys Met Val Asp Pro Lys Gly
    450                 455                 460

Phe Ser Lys Ser Ser Thr Leu Glu Asn Thr Val Asn Gly Ala Pro Gly
465                 470                 475                 480

Ile Glu Ala Ala Phe Cys Lys Asn Pro Asn Lys Leu Phe Gly Val Gly
                485                 490                 495

Pro Ser Asp Ile Asp Lys Tyr Ser Arg Val Val Phe Pro Val Cys Phe
            500                 505                 510

Val Cys Phe Gly Leu Met Tyr Trp Ile Ile Tyr Leu His Val Ser Asp
        515                 520                 525

Val Leu Pro Asp Asp Val Gly Asp Asp
    530                 535

<210> SEQ ID NO 4
<211> LENGTH: 1614
<212> TYPE: DNA
<213> ORGANISM: Dermacentor variabilis

<400> SEQUENCE: 4
atgagacaag cgatggcgtt cagttgctgg tccttcgttc tcttcgtggc cgtcgctgtc    60
accagtgccg gtcgggataa tggtccagcc cccctgcggc cgggacaaac gcaacgtgga   120
```

-continued

```
caaaacatca cgcagattct gaatgccttc tttacacgtg ggtacgacag gagggtgagg    180
ccaaattatg gcggcgttcc agtggaagtt ggcgtcacta tgcagattat cagcataagt    240
acagtctctg aagtacaaat ggactttact tctgacttct atttccggca atcgtggcgg    300
gacgagcgac tctcgttcca gaaaagccca gacctcgaga gcatgactgt gggcgctgaa    360
gtggccgaga ggatctgggt acccgacacc ttcttcgcca acgagaagag cgcctacttt    420
catgcggcca caacgcccaa cactttcctc cgcatcggct ccggaggaga ggttttccgc    480
agtattcgac tgacggtgac tgccagctgc ccaatggatc tcagatactt cccgatggac    540
agacaagcgt gcactataga gatagaaagc tttggttata ccatgaaaga catccgctac    600
cggtggtcgg acggtgacac ctccgtccgc atcgccaagg aggtagagtt gccgcagttc    660
aaggtcctcg gtcacgtcca aaaagccaaa gaggttgccc taacgacagg aaactactcc    720
cgcctggtat gtgaaatacg gttcgcccgc tccatgggct actacctgat ccagatctac    780
atcccggccg gattgatcgt ggttatttcc tgggtctcct tttggctcca ccgtgacgct    840
agtccagctc gcgtcgcgct cggcgtcacc accgtgctca cgatgaccac actcatgtcc    900
agtaccaacg cagcgctgcc caaaatatcc tacgtcaaga gtatcgacgt ctacctgggc    960
acatgtttcg taatggtgtt taccgcgctc ctggagtacg ccgcggtagg atatctcggc   1020
aagagaatca ccatgaggaa aacccgctgt cagcagctgg caaaacttgc agagcaacac   1080
aggcagagat gcgccgcggc ttcttccaac gagccaagct ctgagccctt gctagccagt   1140
cctgaagtat ccattgtcaa gacggtcggt tcctgtcaag tttgtcctgc tgcggtggca   1200
tcccaaggac aaccgaggga agcaccacca accggattta ccatgggtcg cagaggcgca   1260
gaccaatgtt gccctggtct ccagggttca tgtcaggtct gccccgctgc ggtcgcctca   1320
caaacccaac aacaggctcc tccaccaggg atacctatgg aagtacgtct caaaatggtt   1380
gaccccaagg gattcagcaa atcctcgact ctggagaaca ccgtcaacgg cgcgccggac   1440
atcgaggcag cgttttgcaa gaaccccaac aaattatttg gcgtcggccc ttccgatatc   1500
gacaagtact cccgagtggt gttccccgtt tgcttcgtct gtttcgacct catgtactgg   1560
atcatttacc tgcacatcag cgacgttctg ccggacgacg tcggcgacga ctag          1614
```

<210> SEQ ID NO 5
<211> LENGTH: 1614
<212> TYPE: DNA
<213> ORGANISM: Dermacentor variabilis

<400> SEQUENCE: 5

```
atgagacaag cgatggcgtt cagttgctgg tccttcgttc tcttcgtggc cgtcgctgtc     60
accagtgccg gtcgggataa tggtccagcc cccctgcggc cgggacaaac gcaacgtgga    120
caaaacatca cgcagattct gaatgccttc tttacacgtg ggtacgacag gagggtgagg    180
ccaaattatg gcggcgttcc agtggaagtt ggcgtcacta tgcagattat cagcataagt    240
acagtctctg aagtacaaat ggactttact tctgacttct atttccggca atcgtggcgg    300
gacgagcgac tctcgttcca gaaaagccca gacctcgaga gcatgactgt gggcgctgaa    360
gtggccgaga ggatctgggt acccgacacc ttcttcgcca acgagaagag cgcctacttt    420
catgcggcca caacgcccaa cactttcctc cgcatcggct ccggaggaga ggttttccgc    480
agtattcgac tgacggtgac tgccagctgc ccaatggatc tcagatactt cccgatggac    540
agacaagcgt gcactataga gatagaaagc tttggttata ccatgaaaga catccgctac    600
cggtggtcgg acggtgacac gtccgtccgc atcgccaagg aggtagagtt gccgcagttc    660
```

-continued

```
aaggtcctcg gtcacgtcca aaaagccaaa gaggttgccc taacgacagg aaactactcc    720
cgcctggtat gtgaaatacg gttcgcccgc tccatgggct actacctgat ccagatctac    780
atcccggccg gattgatcgt ggttatttcc tgggtctcct tttggctcca ccgtaacgct    840
agtccagctc gcgtcgcgct cggcgtcacc accgtgctca cgatgaccac actcatgtcc    900
agtaccaacg cagcgctgcc caaaatatcc tacgtcaaga gtatcgacgt ctacctgggc    960
acatgtttcg taatggtgtt taccgcgctc ctggagtacg ccgcggtagg atatctcggc   1020
aagagaatca ccatgaggaa aacccgctgt cagcagctgg caaaacttgc agagcaacac   1080
aggcagagat gcgccgcagc ttcttccaac gagccaagct ctgagccctt gctagccagt   1140
cctgaagtat ccattgtcaa gacggtcggt tcctgtcaag tttgtcctgc tgcggtggca   1200
tcccaaggac aaccgaggga agcaccacca accggattta ccatgggtcg cagaggcgca   1260
gaccaatgtt gccctggtct ccagggttca tgtcaggtct gccccgctgc ggtcgcctca   1320
caaacccaac aacaggctcc tccaccaggg atacctatgg aagtacgtct caaaatggtt   1380
gaccccaagg gattcagcaa atcctcgact ctggagaaca ccgtcaacgg cgcgccggac   1440
atcgaggcag cgttttgcaa gaaccccaac aaattatttg gcgtcggccc ttccgatatc   1500
gacaagtact cccgagtggt gttccccgtt tgcttcgtct gtttcgacct catgtactgg   1560
atcatttacc tgcacatcag cgacgttctg ccggacgacg tcggcgacga ctag         1614
```

<210> SEQ ID NO 6
<211> LENGTH: 1614
<212> TYPE: DNA
<213> ORGANISM: Dermacentor variabilis

<400> SEQUENCE: 6

```
atgagacaag cgatggcgtt cagttgctgg tccttcgttc tcttcgtggc cgtcgctgtc     60
accagtgccg gtcgggataa tggtccagcc cccctgcggc cgggacaaac gcaacgtgga    120
caaaacatca cgcagattct gaatgccttc tttacacgtg ggtacgacag gagggtgagg    180
ccaaattatg gcggcgttcc agtggaagtt ggcgtcacta tgcagattat cagcataagt    240
acagtctctg aagtacaaat ggactttact tctgacttct atttccggca atcgtggcgg    300
gacgagcgac tctcgttcca gaaaagccca gacctcgaga gcatgactgt gggcgctgaa    360
gtggccgaga ggatctgggt acccgacacc ttcttcgcca acgagaagag cgcctacttt    420
catgcggcca caacgcccaa cactttcctc cgcatcggct ccggaggaga ggttttccgc    480
agtattcgac tgacggtgac tgccggctgc ccaatggatc tcagatactt cccgatggac    540
agacaagcgt gcactataga gatagaaagc tttggttata ccatgaaaga catccgctac    600
cggtggtcgg acggtgacac ctccgtccgc atcgccaagg aggtagagtt gccgcagttc    660
aaggtcctcg gtcacgtcca aaaagccaaa gaggttgccc taacgacagg aaactactcc    720
cgcctggtat gtgaaatacg gttcgcccgc tccatgggct actacctgat ccagatctac    780
atcccggccg gattgatcgt ggttatttcc tgggtctcct tttggctcca ccgtgacgct    840
agtccagctc gcgtcgcgct cggcgtcacc accgtgctca cgatgaccac actcatgtcc    900
agtaccaacg cagcgctgcc caaaatatcc tacgtcaaga gtatcgacgt ctacctgggc    960
acatgtttcg taatggtgtt taccgcgctc ctggagtacg ccgcggtagg atatctcggc   1020
aagagaatca ccatgaggaa aacccgctgt cagcagctgg caaaacttgc agagcaacac   1080
aggcagagat gcgccgcggc ttcttccaac gagccaagct ctgagccctt gctagccagt   1140
```

-continued

```
cctgaggtat ccattgtcaa gacggtcggt tcctgtcggg tttgtcctgc tgcggtggca    1200
tcccaaggac aaccgaggga agcaccacca accggattta ccatgggtcg cagaggcgca    1260
gaccaatgtt gccctggtct ccagggttca tgtcaggtct gccccgctgc ggtcgcctca    1320
caaacccaac aacaggctcc tccaccaggg atacctatgg aagtacgtct caaaatggtt    1380
gaccccaagg gattcagcaa atcctcgact ctggagaaca ccgtcaacgg cgcgccgggc    1440
atcgaggcag cgttttgcaa gaaccccaac aaattatttg gcgtcggccc ttccgatatc    1500
gacaagtact cccgagtggt gttccccgtt tgcttcgtct gtttcggcct catgtactgg    1560
atcatttacc tgcacgtcag cgacgttctg ccggacgacg tcggcgacga ctag          1614
```

<210> SEQ ID NO 7
<211> LENGTH: 606
<212> TYPE: PRT
<213> ORGANISM: Dermacentor melanogaster

<400> SEQUENCE: 7

```
Met Ser Asp Ser Lys Met Asp Lys Leu Ala Arg Met Ala Pro Leu Pro
 1               5                  10                  15

Arg Thr Pro Leu Leu Thr Ile Trp Leu Ala Ile Asn Met Ala Leu Ile
             20                  25                  30

Ala Gln Glu Thr Gly His Lys Arg Ile His Thr Val Gln Ala Ala Thr
         35                  40                  45

Gly Gly Gly Ser Met Leu Gly Asp Val Asn Ile Ser Ala Ile Leu Asp
     50                  55                  60

Ser Phe Ser Val Ser Tyr Asp Lys Arg Val Arg Pro Asn Tyr Gly Gly
 65                  70                  75                  80

Pro Pro Val Glu Val Gly Val Thr Met Tyr Val Leu Ser Ile Ser Ser
                 85                  90                  95

Val Ser Glu Val Leu Met Asp Phe Thr Leu Asp Phe Tyr Phe Arg Gln
            100                 105                 110

Phe Trp Thr Asp Pro Arg Leu Ala Tyr Arg Lys Arg Pro Gly Val Glu
        115                 120                 125

Thr Leu Ser Val Gly Ser Glu Phe Ile Lys Asn Ile Trp Val Pro Asp
    130                 135                 140

Thr Phe Val Asn Glu Lys Gln Ser Tyr Phe His Ile Ala Thr Thr
145                 150                 155                 160

Ser Asn Glu Phe Ile Arg Val His His Ser Gly Ser Ile Thr Arg Ser
                165                 170                 175

Ile Arg Leu Thr Ile Thr Ala Ser Cys Pro Met Asn Leu Gln Tyr Phe
            180                 185                 190

Pro Met Asp Arg Gln Leu Cys His Ile Glu Ile Glu Ser Phe Gly Tyr
        195                 200                 205

Thr Met Arg Asp Ile Arg Tyr Phe Trp Arg Asp Gly Leu Ser Ser Val
    210                 215                 220

Gly Met Ser Ser Glu Val Glu Leu Pro Gln Phe Arg Val Leu Gly His
225                 230                 235                 240

Arg Gln Arg Ala Thr Glu Ile Asn Leu Thr Thr Gly Asn Tyr Ser Arg
                245                 250                 255

Leu Ala Cys Glu Ile Gln Phe Val Arg Ser Met Gly Tyr Tyr Leu Ile
            260                 265                 270

Gln Ile Tyr Ile Pro Ser Gly Leu Ile Val Val Ile Ser Trp Val Ser
        275                 280                 285

Phe Trp Leu Asn Arg Asn Ala Thr Pro Ala Arg Val Ala Leu Gly Val
```

```
            290                 295                 300
Thr Thr Val Leu Thr Met Thr Thr Leu Met Ser Ser Thr Asn Ala Ala
305                 310                 315                 320

Leu Pro Lys Ile Ser Tyr Val Lys Ser Ile Asp Val Tyr Leu Gly Thr
                325                 330                 335

Cys Phe Val Met Val Phe Ala Ser Leu Leu Glu Tyr Ala Thr Val Gly
                340                 345                 350

Tyr Met Ala Lys Arg Ile Gln Met Arg Lys Gln Arg Phe Met Ala Ile
                355                 360                 365

Gln Lys Ile Ala Glu Gln Lys Lys Gln Gln Leu Asp Gly Ala Asn Gln
        370                 375                 380

Gln Gln Ala Asn Pro Asn Pro Asn Ala Asn Val Gly Gly Pro Gly Gly
385                 390                 395                 400

Val Gly Val Gly Pro Gly Gly Pro Gly Gly Pro Gly Gly Gly Val Asn
                405                 410                 415

Val Gly Val Gly Met Gly Met Gly Pro Glu His Gly His Gly His Gly
                420                 425                 430

His His Ala His Ser His Gly His Pro His Ala Pro Lys Gln Thr Val
        435                 440                 445

Ser Asn Arg Pro Ile Gly Phe Ser Asn Ile Gln Gln Asn Val Gly Thr
450                 455                 460

Arg Gly Cys Ser Ile Val Gly Pro Leu Phe Gln Glu Val Arg Phe Lys
465                 470                 475                 480

Val His Asp Pro Lys Ala His Ser Lys Gly Gly Thr Leu Glu Asn Thr
                485                 490                 495

Val Asn Gly Gly Arg Gly Gly Pro Gln Ser His Gly Pro Gly Pro Gly
                500                 505                 510

Gln Gly Gly Gly Pro Pro Gly Gly Gly Gly Gly Gly Gly Gly Gly Gly
        515                 520                 525

Gly Pro Pro Glu Gly Gly Asp Pro Glu Ala Ala Val Pro Ala His
        530                 535                 540

Leu Leu His Pro Gly Lys Val Lys Lys Asp Ile Asn Lys Leu Leu Gly
545                 550                 555                 560

Ile Thr Pro Ser Asp Ile Asp Lys Tyr Ser Arg Ile Val Phe Pro Val
                565                 570                 575

Cys Phe Val Cys Phe Asn Leu Met Tyr Trp Ile Ile Tyr Leu His Val
                580                 585                 590

Ser Asp Val Val Ala Asp Asp Leu Val Leu Leu Gly Glu Glu
        595                 600                 605

<210> SEQ ID NO 8
<211> LENGTH: 3385
<212> TYPE: DNA
<213> ORGANISM: Dermacentor melanogaster

<400> SEQUENCE: 8
atgagatgag tgattcaaaa atggacaagc tggcccggat ggcgcccctg ccccgacaag       60
cgatggcgtt cagttgctgg tccttcgttc tcttcgtggc cgtcgcacac cgctgctaac      120
catctggctg ccatcaaca tggccctgat tgcacctgtc accagtgccg gtcgggataa      180
tggtccagcc cccctgcggc cgaggaaacg ggccacaaac ggatccatac agtgcaagcg      240
gcgactggcg gtggacaaac gcaacgtgga caaaacatca cgcagattct gaatgccttc      300
ttggcagcat gctgggtgac gtaaacatat ccgctattct cgactccttt acacgtgggt      360
```

-continued

| | |
|---|---|
| acgacaggag ggtgaggcca aattatggcg gcgttccagt agtgttagtt acgacaaaag | 420 |
| agtaagaccc aattacggtg gtcccnctgt ggaagttggc gtcactatgc agattatcag | 480 |
| cataagtaca gtctctgaat ggaggttggc gtcacaatgt atgtcctcag tatcagttcg | 540 |
| gtttcggaag tacaaatgga ctttacttct gacttctatt tccggcaatc gtggcgggag | 600 |
| ttctaatgga cttcacattg gatttttact ttcgtcaatt ttggaccgac gagcgactct | 660 |
| cgttccagaa aagcccagac ctcgagagca tgactgtggt cctcgtttag cgtatagaaa | 720 |
| acgacctggt gtagaaacac tatcggttgg cgctgaagtg gccgagagga tctgggtacc | 780 |
| cgacaccttc ttcgccaacg atcagagttc attaagaata tttgggtacc tgacaccttt | 840 |
| tttgtaaatg agaagagcgc ctactttcat gcggccacaa cgcccaacac tttcctccgg | 900 |
| aaaaacaatc atattttcac attgcaacaa ccagtaatga attcatacgc atcggctccg | 960 |
| gaggagaggt tttccgcagt attcgactga cggtgactgt gtgcatcatt ctggatcgat | 1020 |
| aacaagaagt attagattga ctataaccgc cagctgccca atggatctca gatacttccc | 1080 |
| gatggacaga caagcgtgcc atcgtgtccg atgaatctac aatatttccc catggatcgc | 1140 |
| cagctgtgca ctatagagat agaaagcttt ggttatacca tgaaagacat ccgctaccgc | 1200 |
| acattgaaat cgaaagcttc ggttacacga tgcgagatat ccgatatttg tggtcggacg | 1260 |
| gtgacacgtc cgtccgcatc gccaaggagg tagagttgcc tggagagatg gactgagtag | 1320 |
| tgttggcatg agcagtgagg tcgaactacc gcagttcaag gtcctcggtc acgtccaaaa | 1380 |
| agccaaagag gttgccctac gcagttccga gttttgggac acaggcagag ggcgaccgaa | 1440 |
| ataaacctaa cgacaggaaa ctactcccgc ctggtatgtg aaatacggtt cgcccgctca | 1500 |
| ccacaggcaa ctattcgcgt ttagcctgcg aaattcagtt cgtgcgttcc atgggctact | 1560 |
| acctgatcca gatctacatc ccggccggat tgatcgtggg atgggctact accttataca | 1620 |
| aatctacata ccctctggac tgatcgttgt tatttcctgg gtctcctttt ggctccaccg | 1680 |
| taacgctagt ccagctcgct tatatcatgg gtatcatttt ggctcaatcg caatgcaacg | 1740 |
| ccggcgcgtg tcgcgctcgg cgtcaccacc gtgctcacga tgaccacact catgtccagg | 1800 |
| tggcgctcgg tgtgacaacc gtgttgacaa tgaccacttt gatgtcgtct accaacgcag | 1860 |
| cgctgcccaa aatatcctac gtcaagagta tcgacgtcta acaaatgcag cgctgccaaa | 1920 |
| gatttcgtac gtcaaatcga ttgacgtcta cctgggcaca tgtttcgtaa tggtgtttac | 1980 |
| cgcgctcctg gagtacgcca tctgggaaca tgcttcgtta tggtctttgc cagtctactg | 2040 |
| gaatacgccg cggtaggata tctcggcaag agaatcacca tgaggaaaac ccgctgtcaa | 2100 |
| cggtcggcta catggcaaaa cgaattcaaa tgcgaaaaca agatttatg cagctggcaa | 2160 |
| aacttgcaga gcaacacagg cagagatgcg ccgcagctgg cgatccaaaa gatagccgaa | 2220 |
| cagaaaaagc aacagctcga cggagcgatc ttccaacgag ccaagctctg agcccttgct | 2280 |
| agccagtcct gaagtatcac caacagcagg cgaatcccaa tcccaatgca aatgtgggcg | 2340 |
| gacccggaca ttgtcaagac ggtcggttcc tgtcaagttt gtcctgctgc ggtggcatgg | 2400 |
| agtgggcgtt ggaccggcg gacccggagg acccggtggc ggggtcaacc caaggacaac | 2460 |
| cgagggaagc accaccaacc ggatttacca tgggtctgtg ggcgtcggta tgggcatggg | 2520 |
| accgaacat ggccacgggc atggacgcag aggcgcagac caatgttgcc ctggtctcca | 2580 |
| gggttcatgt caggtcacca cgcccacagc catggacatc cgcatgcgcc caagcaaaca | 2640 |
| gtgagttgcc ccgctgcggt cgcctcacaa acccaacaac aggctcctcc accaggaacc | 2700 |
| gcccaatcgg cttttccaat atccaacaaa acgttggtac gcgcgggata cctatggaag | 2760 |

-continued

```
tacgtctcaa atggttgtt gctcgatagt gggacccttg ttccaggagg tgagattcaa    2820
ggtccacgac cccaagggat tcagcaaatc ctcgactctg agaacaccg tcaacggcac    2880 ccgaaggccc actccaaggg cggaacgctg gagaatacgg tgaatggcgc gccggggacg    2940
cggtggtccg caatcgcatg gaccgggtcc gggccaaggc ggcggacatc gaggcagcga    3000
ccgcccggcg gtggcggagg cggtggaggc ggggcggac cgcccgaggt tttgcaagaa    3060
ccccaacaaa ttatttggcg tcggcccttc cgatataaag taaaaaggga catcaacaag    3120
ctgctgggca tcacgccctc cgacatcgac aagtactccc gagtggtgtt ccccgtttgc    3180
ttcgtctgtt tcgacccgac aagtactcac gcatcgtgtt ccccgtgtgc tttgtgtgct    3240
tcaacctcat gtactggatc atttacctgc acatcagcga cgttctgccg gacgatgatg    3300
tactggatca tttacctgca tgtcagcgac gtggtcgccg atgatcgtcg gcgacgacta    3360
gctggtgctt ctgggcgagg agtag                                          3385
```

<210> SEQ ID NO 9
<211> LENGTH: 10
<212> TYPE: PRT
<213> ORGANISM: Artificial Sequence
<220> FEATURE:
<223> OTHER INFORMATION: Segment from dermacentor variabilis

<400> SEQUENCE: 9

Gln Ile Leu Asn Ala Phe Phe Thr Arg Gly
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Segment from dermacentor variabilis

<400> SEQUENCE: 10

Met Thr Val Gly Ala Glu Val Ala Glu Arg Ile Trp Val Pro
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Segment from dermacentor variabilis

<400> SEQUENCE: 11

Arg Trp Ser Asp Gly Asp Thr Ser Val Arg Ile Ala Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Segment from dermacentor variabilis

<400> SEQUENCE: 12

Thr Ala Leu Leu Glu Tyr Ala Ala Val Gly Tyr Leu Gly
1               5                   10

<210> SEQ ID NO 13
<211> LENGTH: 26
<212> TYPE: PRT

<213> ORGANISM: Artificial Sequence
<220> FEATURE:
<223> OTHER INFORMATION: Segment from dermacentor variabilis

<400> SEQUENCE: 13

Arg Cys Ala Ala Ala Ser Ser Asn Glu Pro Ser Ser Glu Pro Leu Leu
1               5                   10                  15

Ala Ser Pro Glu Val Ser Ile Val Lys Thr
            20                  25

<210> SEQ ID NO 14
<211> LENGTH: 11
<212> TYPE: PRT
<213> ORGANISM: Artificial Sequence
<220> FEATURE:
<223> OTHER INFORMATION: Segment from dermacentor variabilis

<400> SEQUENCE: 14

Gln Pro Arg Glu Ala Pro Pro Thr Gly Phe Thr
1               5                   10

<210> SEQ ID NO 15
<211> LENGTH: 20
<212> TYPE: PRT
<213> ORGANISM: Artificial Sequence
<220> FEATURE:
<223> OTHER INFORMATION: Segment from dermacentor variabilis

<400> SEQUENCE: 15

Met Gly Arg Arg Gly Ala Asp Gln Cys Cys Pro Gly Leu Gln Gly Ser
1               5                   10                  15

Cys Gln Val Cys
            20

<210> SEQ ID NO 16
<211> LENGTH: 17
<212> TYPE: PRT
<213> ORGANISM: Artificial Sequence
<220> FEATURE:
<223> OTHER INFORMATION: Segment from dermacentor variabilis

<400> SEQUENCE: 16

Met Glu Val Arg Leu Lys Met Val Asp Pro Lys Gly Phe Ser Lys Ser
1               5                   10                  15

Ser

<210> SEQ ID NO 17
<211> LENGTH: 13
<212> TYPE: PRT
<213> ORGANISM: Artificial Sequence
<220> FEATURE:
<223> OTHER INFORMATION: Segment from dermacentor variabilis

<400> SEQUENCE: 17

His Ile Ser Asp Val Leu Pro Asp Asp Val Gly Asp Asp
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Segment from dermacentor variabilis

<400> SEQUENCE: 18

```
His Val Ser Asp Val Leu Pro Asp Asp Val Gly Asp Asp
  1               5                  10
```

<210> SEQ ID NO 19
<211> LENGTH: 25
<212> TYPE: PRT
<213> ORGANISM: Artificial Sequence
<220> FEATURE:
<223> OTHER INFORMATION: Segment from dermacentor variabilis

<400> SEQUENCE: 19

```
Leu Gly Lys Arg Ile Thr Met Arg Lys Thr Arg Cys Gln Gln Leu Ala
  1               5                  10                  15

Lys Leu Ala Glu Gln His Arg Gln Arg
             20                  25
```

<210> SEQ ID NO 20
<211> LENGTH: 18
<212> TYPE: DNA
<213> ORGANISM: Artificial Sequence
<220> FEATURE:
<223> OTHER INFORMATION: Segment from dermacentor variabilis

<400> SEQUENCE: 20
caaacgcaac gtggacaa                                                       18

<210> SEQ ID NO 21
<211> LENGTH: 18
<212> TYPE: DNA
<213> ORGANISM: Artificial Sequence
<220> FEATURE:
<223> OTHER INFORMATION: Segment from dermacentor variabilis

<400> SEQUENCE: 21
gagcgactct cgttccag                                                       18

<210> SEQ ID NO 22
<211> LENGTH: 18
<212> TYPE: DNA
<213> ORGANISM: Artificial Sequence
<220> FEATURE:
<223> OTHER INFORMATION: Segment from dermacentor variabilis

<400> SEQUENCE: 22
atcggctccg gaggagag                                                       18

<210> SEQ ID NO 23
<211> LENGTH: 24
<212> TYPE: DNA
<213> ORGANISM: Artificial Sequence
<220> FEATURE:
<223> OTHER INFORMATION: Segment from dermacentor variabilis

<400> SEQUENCE: 23
aaggtcctcg gtcacgtcca aaaa                                                24

<210> SEQ ID NO 24
<211> LENGTH: 18
<212> TYPE: DNA
<213> ORGANISM: Artificial Sequence
<220> FEATURE:
<223> OTHER INFORMATION: Segment from dermacentor variabilis

<400> SEQUENCE: 24
ctcggcaaga gaatcacc                                                       18

<210> SEQ ID NO 25
<211> LENGTH: 18
<212> TYPE: DNA
<213> ORGANISM: Artificial Sequence
<220> FEATURE:
<223> OTHER INFORMATION: Segment from dermacentor variabilis

<400> SEQUENCE: 25
ggttcctgtc aagtttgt                                                   18

<210> SEQ ID NO 26
<211> LENGTH: 18
<212> TYPE: DNA
<213> ORGANISM: Artificial Sequence
<220> FEATURE:
<223> OTHER INFORMATION: Segment from dermacentor variabilis

<400> SEQUENCE: 26
ggttcctgtc gggtttgt                                                   18

<210> SEQ ID NO 27
<211> LENGTH: 18
<212> TYPE: DNA
<213> ORGANISM: Artificial Sequence
<220> FEATURE:
<223> OTHER INFORMATION: Segment from dermacentor variabilis

<400> SEQUENCE: 27
ccaaccggat ttaccatg                                                   18

<210> SEQ ID NO 28
<211> LENGTH: 1197
<212> TYPE: DNA
<213> ORGANISM: Artificial Sequence
<220> FEATURE:
<223> OTHER INFORMATION: Rhipicephalus probe

<400> SEQUENCE: 28
cggatattgg acagcatcat tggccagggt cgttatgact gcaggatccg gcccatggga        60
attaacaaca cagacgggcc ggctcttgta cgcgttaaca tctttgtaag aagtatcggc       120
agaattgatg acgtcaccat ggagtacaca gtgcaaatga cgttcagaga gcagtggcgg       180
gacgagagac tccagtacga cgacttgggc ggccaggttc gctacctgac gctcaccgaa       240
ccggacaagc tttggaagcc ggacctgttt ttctccaacg agaaagaggg acacttccac       300
aacatcatca tgcccaacgt gcttctacgc atacatccca acggcgacgt tctcttcagc       360
atcagaatat ccttggtgct ttcatgtccg atgaacctga aattttatcc tttggataaa       420
caaatctgct ctatcgtcat ggtgagctat ggtatacaa cagaggacct ggtgtttcta       480
tggaaagagg gggatcctgt acaggtcaca aaaaatctcc acttgccacg tttcacgctg       540
gaaaggtttc aaaccgacta ctgcaccagt cggaccaaca ctggcgagta cagctgcttg       600
cgcgtggacc tggtgttcaa gcgcgagttc agctactacc tgatccagat ctacatcccg       660
tgctgcatgc tggtcatcgt gtcctgggtg tcgttctggc tcgacccac tcgatcccg       720 gcgcgagtgt cgctgggcgt caccacctg ctcaccatgg ccacgcagat atcgggcatc       780
aacgcctcgc tgcctcccgt ttcctacacc aaggccattg acgtgtggac cggcgtctgt       840
ctgaccttcg tattcggcgc gctcctcgag ttcgccctgg tcaactacgc ctcgcggtca       900
gattcacgcc ggcagaacat gcagaagcag aagcagagga aatgggagct cgagccgccc       960
ctggactcgg accacctgga ggacggcgcc accacgttcg ccatgaggcc gctggtgcac      1020

-continued

```
caccacggag agctgcatgc cgacaagttg cggcagtgcg aagtccacat gaagaccccc    1080
aagacgaacc tttgcaaggc ctggctttcc aggtttccca cgcgatccaa acgcatcgac    1140
gtcgtctcgc ggatcttctt tccgctcatg ttcgccctct tcaacctcgt ctactgg       1197
```